(12) United States Patent
Parker et al.

(10) Patent No.: US 9,169,229 B2
(45) Date of Patent: Oct. 27, 2015

(54) METHOD FOR PRODUCING PURIFIED DIALKYL-FURAN-2,5-DICARBOXYLATE BY PHYSICAL SEPARATION AND SOLID LIQUID SEPARATION

(71) Applicant: Eastman Chemical Company, Kingsport, TN (US)

(72) Inventors: Kenny Randolph Parker, Afton, TN (US); Ashfaq Shaikh, Kingsport, TN (US); Lee Reynolds Parton, Kingsport, TN (US); Mesfin Ejerssa Janka, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/536,387

(22) Filed: Nov. 7, 2014

(65) Prior Publication Data

US 2015/0065735 A1    Mar. 5, 2015

Related U.S. Application Data

(62) Division of application No. 13/530,765, filed on Jun. 22, 2012, now Pat. No. 8,912,349.

(51) Int. Cl.
 *C07D 307/68* (2006.01)
 *C07D 307/46* (2006.01)

(52) U.S. Cl.
 CPC ............ *C07D 307/68* (2013.01); *C07D 307/46* (2013.01)

(58) Field of Classification Search
 CPC ..................................................... C07D 307/68
 USPC ........................................................ 549/485
 See application file for complete search history.

(56) References Cited

U.S. PATENT DOCUMENTS

| | | | |
|---|---|---|---|
| 2,551,731 A | 5/1951 | Drewitt | |
| 3,225,066 A | 12/1965 | Lew | |
| 3,845,100 A | 10/1974 | Kusak | |
| 3,852,247 A | 12/1974 | Vizurraga | |
| 4,405,736 A | 9/1983 | Kubota et al. | |
| 4,876,327 A | 10/1989 | Vriesema et al. | |
| 4,977,283 A | 12/1990 | Leupold et al. | |
| 5,958,581 A | 9/1999 | Khanarian et al. | |
| 5,959,066 A | 9/1999 | Charbonneau et al. | |
| 6,025,061 A | 2/2000 | Khanarian et al. | |
| 6,063,464 A | 5/2000 | Charbonneau et al. | |
| 6,063,465 A | 5/2000 | Charbonneau et al. | |
| 6,063,495 A | 5/2000 | Charbonneau et al. | |
| 6,103,825 A | 8/2000 | Frischinger et al. | |
| 6,107,447 A | 8/2000 | Kreuder et al. | |
| 6,126,992 A | 10/2000 | Khanarian et al. | |
| 6,140,422 A | 10/2000 | Khanarian et al. | |
| 6,342,300 B1 | 1/2002 | Bengs et al. | |
| 6,359,070 B1 | 3/2002 | Khanarian et al. | |
| 6,737,481 B1 | 5/2004 | Kurian et al. | |
| 6,914,120 B2 | 7/2005 | Germroth et al. | |
| 7,052,764 B2 | 5/2006 | Chang et al. | |
| 7,385,081 B1 | 6/2008 | Gong | |
| 7,638,592 B2 | 12/2009 | Benecke et al. | |
| 7,700,788 B2 | 4/2010 | Lilga et al. | |
| 8,143,355 B2 | 3/2012 | Matsuda et al. | |
| 8,658,810 B2 | 2/2014 | Shaikh et al. | |
| 2003/0055271 A1 | 3/2003 | Grushin et al. | |
| 2006/0205977 A1 | 9/2006 | Sumner et al. | |
| 2008/0081883 A1 | 4/2008 | King, II et al. | |
| 2008/0182944 A1 | 7/2008 | Benecke et al. | |
| 2009/0018264 A1 | 1/2009 | Fuseya | |
| 2009/0124829 A1 | 5/2009 | Gong | |
| 2009/0143602 A1 | 6/2009 | Benecke et al. | |
| 2009/0156841 A1 | 6/2009 | Sanborn et al. | |
| 2010/0081774 A1 | 4/2010 | Benecke et al. | |
| 2010/0174044 A1 | 7/2010 | Eritate | |
| 2010/0210867 A1 | 8/2010 | Bustamante et al. | |
| 2010/0331568 A1 | 12/2010 | Brandvold | |
| 2012/0123085 A1 | 5/2012 | Grushin et al. | |

FOREIGN PATENT DOCUMENTS

| | | |
|---|---|---|
| CA | 2235270 | 4/1997 |
| CS | 87340 | 7/1959 |
| EP | 0741134 | 11/1996 |

(Continued)

OTHER PUBLICATIONS

Gandini Alessandro, et al., The Furan Counterpart of Poly(ethylene Terephthalate): An Alternative Material Based on Renewable Resources, Journal of Polymer Science: Part A: Polymer Chemistry, vol. 47, (2009), pp. 295-298.

Partenheimer, Walt et al., Synthesis of 2,5-Diformylfuran and Furan-2,5-Dicarboxylic Acid by Catalytic Air-Oxidation of 5-Hydroxymethylfurfural. Unexpectedly Selective Aerotic Oxidation of Benzyl Alcohol to Benzaldehyde with Metal/Bromide Catalysts, Adv. Synth. Catal. 2001, 343, pp. 102-111.

Lewkowski, J., Synthesis, Chemistry and Applications of 5-Hydroxymethylfurfural and its Derivatives, Arkivoc, 2001, pp. 17-54.

Manasek et al., Modified Fiber-Forming Polyesters From 2,5-Furandicarboxylic Acid, 1963, 6, 35, Chem. Abstract 1964, 60, p. 8180a.

(Continued)

*Primary Examiner* — Taofiq A Solola
(74) *Attorney, Agent, or Firm* — Phan Law Group PLLC

(57) ABSTRACT

A process to produce a purified dimethyl-furan-2,5-dicarboxylate (DMFD) by feeding furan dicarboxylic acid and methanol to an esterification zone to generate a crude diester composition, and purifying the crude diester composition with a physical separation process followed by crystallization, solid liquid separation, and optionally drying to produce a purified DMFD composition. A portion of the stream generated by solid liquid separation can be dissolved and subjected to crystallization and solid liquid separation repeatedly. The process is useful to produce a purified DMFD composition having a low b*, at least 98 wt. % DAFD solids, and a low concentration of 5-(methoxycarbonyl)furan-2-carboxylic acid (MCFC) and methyl 5-formylfuran-2-carboxylate (MFFC).

4 Claims, 4 Drawing Sheets

(56) References Cited

FOREIGN PATENT DOCUMENTS

| | | |
|---|---|---|
| FR | 2723946 | 3/1996 |
| JP | 2008291243 | 12/2008 |
| JP | 2008291244 | 12/2008 |
| JP | 2008308578 | 12/2008 |
| JP | 2009215467 | 9/2009 |
| JP | 2009242312 | 10/2009 |
| JP | 2009263509 | 11/2009 |
| SU | 162962 | 5/1964 |
| WO | 2009118377 | 10/2009 |
| WO | 2009135921 | 11/2009 |
| WO | 2010077133 | 7/2010 |
| WO | 2010132740 | 11/2010 |
| WO | 2010140599 | 12/2010 |
| WO | 2010151346 | 12/2010 |
| WO | 2011023590 | 3/2011 |
| WO | 2011043660 | 4/2011 |
| WO | 2011043661 | 4/2011 |
| WO | 2012101015 | 8/2012 |

OTHER PUBLICATIONS

Rodivilova, et al., Synthesis and Study of Aromatic Polyesters Based on 2,5-Furandicarboxylic Acid and Diphenylolpropane, Tekhnol. 11 1968, 7, 818, Chem. Abstr. 1969, 70, p. 4685v.

Office Action dated Oct. 31, 2013 for Copending U.S. Appl. No. 13/530,789, filed Jun. 22, 2012, Lee Reynolds Partin, et al., 11 pages.

Office Action dated Jul. 26, 2013 for Copending U.S. Appl. No. 13/530,738, filed Jun. 22, 2012, Ashfaq Shaikh, 6 pages.

Lewkowski, J., Convenient Synthesis of Furan-2,5-dicarboxylic Acid and its Derivatives, Polish J. Chem., 75, pp. 1943-1946, (2011).

Haworth, W.N. et al., The Conversion of Sucrose into Furan Compound, Part II, Some 2: 5-Disubstituted Tetrahydrofurans and their Products of Ring Scission, Journal of the Chemical Society, No. 1, (1945), pp. 1-4.

Gonis, George et al., The Preparation fo Furan-2,5-dicarboxylic acid, J. Org. Chem., vol. 27, No. 8 (1962), pp. 2946-2947.

Search Report and Written Opinion for Copending PCT Application No. PCT/US2013/044919, dated Aug. 22, 2013.

Search Report and Written Opinion for Copending PCT Application No. PCT/US2013/044922, dated Sep. 23, 2013.

Sanderson, R D et al., Synthesis and Evaluation of Dialkyl Furan-2,5-Dicarboxylates as Plasticizers for PVC, Journal of Applied Polymer Science, vol. 53, No. 13, (1994), pp. 1785-1793.

Yoder, P A et al., Ueber Dehydroshleimsaure: eine neue Darstellungsmethode, sowie verschiedene Salze und Ester derselben, Berichte Der Deutschen Chemischen Gesellschaft Abteilung B: Abhandlungen, vol. 34, No. 3, (1901), pp. 3446-3462.

Search Report and Written Opinion for Copending PCT Application No. PCT/US2013/044927, dated Oct. 18, 2013.

USPTO Notice of Allownace for Copending U.S. Appl. No. 13/530,738, dated Jan. 22, 2014.

USPTO Office Action for Copending U.S. Appl. No. 13/530,789, dated Apr. 2, 2014.

USPTO Notice of Allowance for Copending U.S. Appl. No. 13/530,789, dated Aug. 25, 2014.

US 9,169,229 B2

METHOD FOR PRODUCING PURIFIED DIALKYL-FURAN-2,5-DICARBOXYLATE BY PHYSICAL SEPARATION AND SOLID LIQUID SEPARATION

1. CROSS-REFERENCE TO RELATED APPLICATIONS

This application is a divisional of U.S. application Ser. No. 13/530,765, filed Jun. 22, 2012. The entire disclosure of the above-referenced application is incorporated herein by reference.

2. FIELD OF THE INVENTION

The invention relates to the processes for the production of purified dialkyl-furan-2,5-dicarboxylate (DAFD) and purified DAFD compositions made therefrom.

3. BACKGROUND OF THE INVENTION

Aromatic dicarboxylic acids such as terephthalic acid and isophthalic acid or their di-esters, dimethyl terephthalate as for example, are used to produce a variety of polyester products, important examples of which are poly (ethylene terephthalate) and its copolymers. The aromatic dicarboxylic acids are synthesized by the catalytic oxidation of the corresponding dialkyl aromatic compounds which are obtained from fossil fuels such as those disclosed in US 2006/0205977 A1. Esterification of these diacids using excess alcohol produces the corresponding di-esters has been disclosed in US2010/0210867A1. There is a growing interest in the use of renewable resources as feed stocks for the chemical industries mainly due to the progressive reduction of fossil reserves and their related environmental impacts.

Furan-2,5-dicarboxylic acid ("FDCA") is a versatile intermediate considered as a promising closest biobased alternative to terephthalic acid and isophthalic acid. Like aromatic diacids, FDCA can be condensed with diols such as ethylene glycol to make polyester resins similar to polyethylene terephthalate (PET) as disclosed in Gandini, A.; Silvestre, A. J; Neto, C. P.; Sousa, A. F.; Gomes, M. *J. Poly. Sci. A* 2009, 47, 295. FDCA has been prepared by oxidation of 5-(hydroxymethyl) furfural (5-HMF) under air using homogenous catalysts as disclosed in US2003/0055271 A1 and in Partenheimer, W.; Grushin, V. V. *Adv. Synth. Catal.* 2001, 343, 102-111. However, achieving high yields has proved difficult. A maximum of 44.8% yield using Co/Mn/Br catalysts system and a maximum of 60.9% yield was reported using Co/Mn/Br/Zr catalysts combination.

The crude FDCA obtained by the oxidation processes must to be purified before they are suitable for end-use applications. JP patent application, JP209-242312A, disclosed crude FDCA purification process using sodium hydroxide/sodium hypochlorite and/or hydrogen peroxide followed by acid treatment of the disodium salt to obtain pure FDCA. This multi-step purification process generates wasteful by-products, is difficult to scale up to a commercial process, and poses safety concerns at large scales.

Therefore, there is a need for an inexpensive and high yield process for the purification of crude FDCA that lends itself more readily to a commercial scale process and lends itself to easy separation step(s).

4. SUMMARY OF THE INVENTION

There is now provided a process for the manufacture of a DAFD composition comprising:
a. feeding a furan-2,5-dicarboxylic acid ("FDCA") composition to an esterification reactor; and
b. in the presence of an alcohol compound, conducting an esterification reaction in the esterification reactor to react FDCA with said alcohol compound to form a crude diester composition comprising dialkyl furan-2,5-dicarboxylate ("DAFD") and the alcohol compound; and
c. separating at least a portion of alcohol compound from the crude diester composition in an alcohol separation zone using a physical separation process to produce a DAFD rich composition comprising DAFD solids, wherein the concentration of DAFD in the DAFD rich composition is higher than the concentration of DAFD in the crude diester composition on a combined solid and liquid basis; and
d. treating the DAFD rich composition in a purification zone to produce a purified DAFD product composition.

There is also provided a process for the preparation of the FDCA fed to the esterification reaction zone.

There is also provided a DAFD composition comprising:
(i) at least 98 wt. % solids based on the weight of the composition, said solids comprising DAFD in an amount of greater than 98 wt. % based on the weight of the solids,
(ii) a b* of 5 or less,
(iii) not more than 3 wt. % 5-(alkoxycarbonyl)furan-2-carboxylic acid (ACFC), and
(iv) not more than 3 wt. % alkyll 5-formylfuran-2-carboxylate (AFFC).

The is also provided a process that forms a very pure DAFD composition on a commercial scale. The process is for the manufacture of a dialkyl furan-2,5-dicarboxylate (DAFD) composition having a throughput of at least 1000 kg/day for any 30 days on a 24 hour/day basis, said process comprising:
a. esterifying furan-2,5-dicarboxylic acid ("FDCA") with an alcohol in an esterification vessel to form a crude diester composition having a b* and comprising unreacted alcohol, water, dialkyl furan-2,5-dicarboxylate ("DAFD"); 5-(alkoxycarbonyl)furan-2-carboxylic acid (ACFC); alkyll 5-formylfuran-2-carboxylate (AFFC); and
b. purifying the crude diester composition to form a purified DAFD product composition, wherein the purified DAFD product composition has:
i. a b* that is lower than the b* of the crude diester composition by at least 1 b* unit; and
ii. a higher DAFD concentration than the DAFD concentration in the crude diester composition by at least 200%; and
iii. a lower ACFC concentration than the concentration of ACFC in the crude diester composition by at least 70%, without taking into account the amount of alcohol in the crude diester composition; and
iv. a lower AFFC concentration than the concentration of AFFC in the crude diester composition by at least 70%.

5. BRIEF DESCRIPTION OF THE DRAWINGS

6. DETAILED DESCRIPTION OF THE INVENTION

Figure 1:
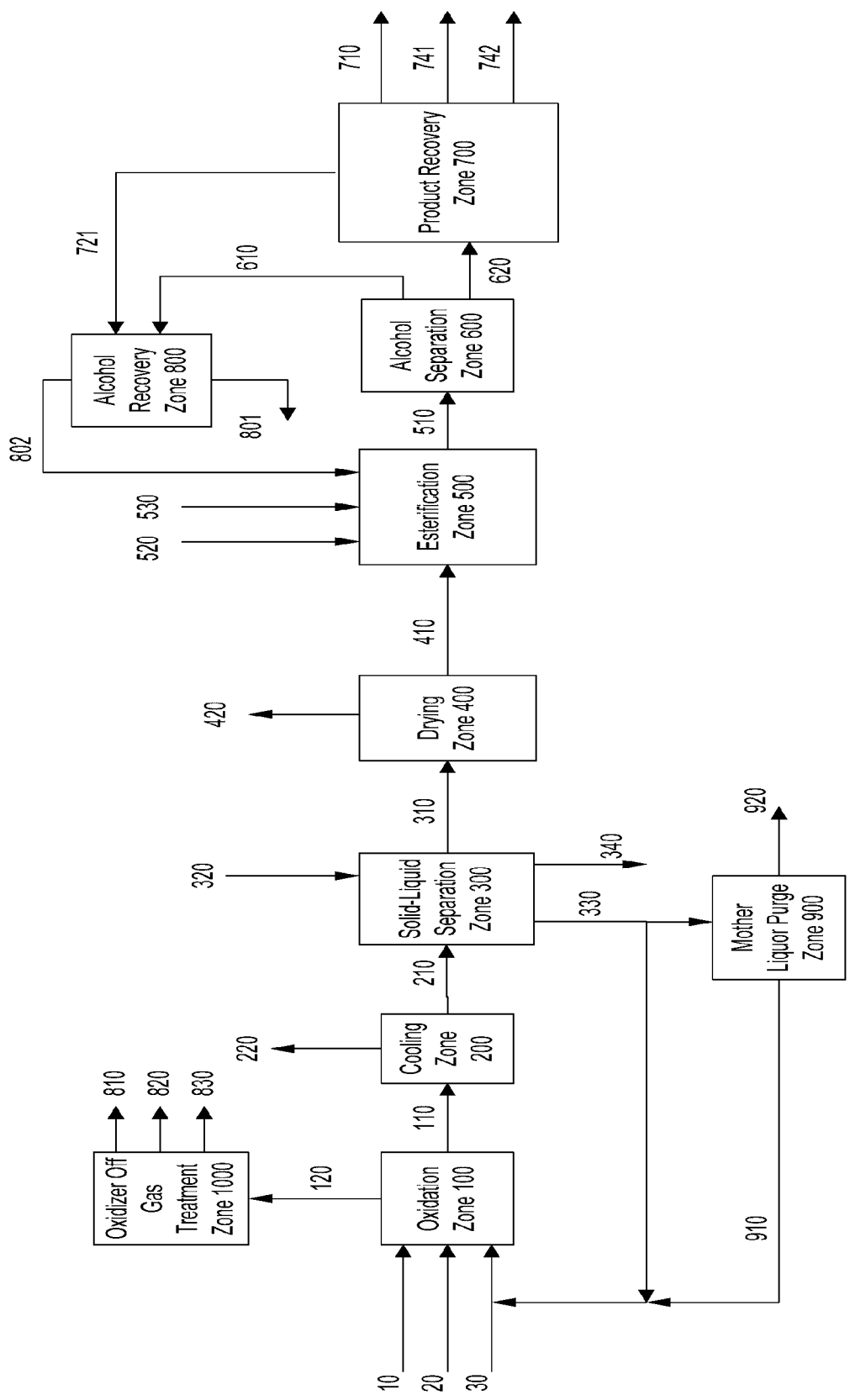
FIG. 1 is a flow diagram of the process for making both FDCA and DAFD.

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. For example, if the specification describes a specific temperature of 62° F., such a description provides literal support for a broad numerical range of 25° F. to 99° F. (62° F.+1-37° F.), an intermediate numerical range of 43° F. to 81° F. (62° F.+1-19° F.), and a narrow numerical range of 53° F. to 71° F. (62° F.+1-9° F.). These broad, intermediate, and narrow numerical ranges should be applied not only to the specific values, but should also be applied to differences between these specific values. Thus, if the specification describes a first pressure of 110 psia and a second pressure of 48 psia (a difference of 62 psia), the broad, intermediate, and narrow ranges for the pressure difference between these two streams would be 25 psia to 99 psia, 43 psia to 81 psia, and 53 psia to 71 psia, respectively The word "rich" in reference to a composition means the concentration of the referenced ingredient in the composition is higher than the concentration of the same ingredient in the feed composition to the separation zone by weight. For example, a DAFD rich composition means that the concentration of DAFD in the DAFD rich composition is greater than the concentration of DAFD in the crude diester stream feeding the separation zone.

All amounts are by weight unless otherwise specified.

As illustrated in FIG. 1, a dicarboxylic acid composition stream 410, which can be either dried carboxylic acid solids or a wet cake containing carboxylic acid, in each case the carboxylic acid comprising furan dicarboxylic acid ("FDCA"), and an alcohol composition stream 520 are fed to the esterification reaction zone 500. The solid dicarboxylic acid composition 410 can be shipped via truck, ship, or rail as solids to a plant or facility for the manufacture of the diester composition. The process for the oxidation of the oxidizable material containing the furan group can be integrated with the process for the manufacture of the diester composition. An integrated process includes co-locating the two manufacturing facilities, one for oxidation and the other for esterification, within 10 miles, or within 5 miles, or within 2 miles, or within 1 mile, or within ½ mile of each other. An integrated process also includes having the two manufacturing facilities in solid or fluid communication with each other. If a solid dicarboxylic acid composition is produced, the solids can be conveyed by any suitable means, such as air or belt, to the esterification facility. If a wet cake dicarboxylic acid composition is produced, the wet cake can be moved by belt or pumped as a liquid slurry to the facility for esterification.

The esterification zone 500 contains at least one esterification reactor vessel. The dicarboxylic acid composition comprising FDCA is fed to the esterification zone and, in the presence of an alcohol compound, an esterification reaction is conducted in an esterification reactor by reacting FDCA with said alcohol compound to form a crude diester composition comprising dialkyl furan-2,5-dicarboxylate ("DAFD"), the alcohol compound, 5-(alkoxycarbonyl)furan-2-carboxylic acid (ACFC), alkyl furan-2-carboxylate (AFC), and alkyl-5-formylfuran-2-carboxylate (AFFC). The crude diester composition may optionally contain a catalyst if a homogeneous esterification catalyst is used.

The alcohol composition is one or more types of alcohol compounds. Examples include compounds represented by the structure R—OH wherein R can range from 1 to 6 carbons, or 1 to 5 carbon atoms, or 1 to 4 carbon atoms, or 1 to 3 carbon atoms, or 1 to 2 carbon atoms, preferably methanol. R can be branched or unbranched, saturated or unsaturated, and cyclic or acyclic. Desirably, R is an unbranched, saturated, acyclic alkyl group. The alcohol composition contains at least 50 wt. %, or at least 60 wt %, or at least 70 wt %, or at least 80 wt. %, or at least 90 wt. %, or at least 95 wt %, or at least 97 wt %, or at least 98 wt. %, or at least 99 wt. % alcohol compounds based on the weight of the alcohol composition. Desirably, the alcohol composition comprises methanol.

The crude diester composition produced in the esterification reactor is the reaction product of at least FDCA with the alcohol composition to produce DAFD, where the alkyl moiety is an alkyl group containing 1 to 6 carbon atoms, and at least a portion of the alkyl moiety corresponds to the alcohol residue. In the case of a reaction between FDCA and methanol, the diester reaction product is dimethyl furan-2,5-dicarboxylate ("DMFD"). The esterification reaction of FDCA with methanol to produce DMFD comprises multiple reaction mechanisms as illustrated below. One reaction mechanism comprises reacting one mole of FDCA with one mole of MeOH to produce a mole of 5-(methoxycarbonyl)furan-2-carboxylic acid (MCFC) and water. One mole of MCFC can then react with one mole of methanol to produce one mole of the desired product DMFD and water. Because both DMFD and MCFC are present in an esterification reaction zone, the crude diester composition will also contain MCFC in addition to the unreacted hydroxyl compounds and DAFD. A commercial process to produce purified DMFD must allow for the separation of DMFD and MCFC downstream of the esterification zone. An example of a batch result for esterification of crude FDCA with methanol is given in the experimental section.

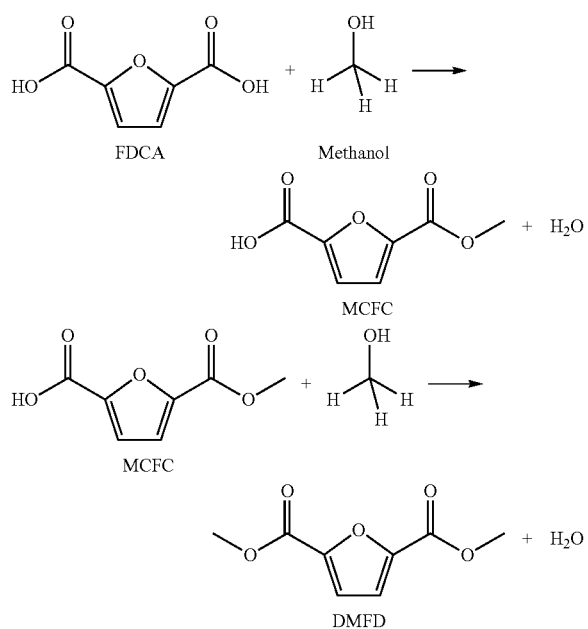

Esterification by-products are also formed in esterification reactor reaction zone 500 and comprise chemicals with boiling points both higher and lower than DMFD. Esterification by-products formed in the esterification reaction zone comprise methyl acetate, alkyl furan-2-carboxylate (AFC), alkyll 5-formylfuran-2-carboxylate (AFFC), and 5-(alkoxycarbonyl)furan-2-carboxylic acid (ACFC). Many other by-products are possible depending upon the impurities contained within the FDCA feedstock. A commercial process to produce a purified DAFD stream must allow for the separation of impurities from the crude di-ester composition exiting as stream 510. Further, at least a portion of these impurities can be purged from the process wherein purging involves isolation of the impurities and routing them from the process.

Figure 2:
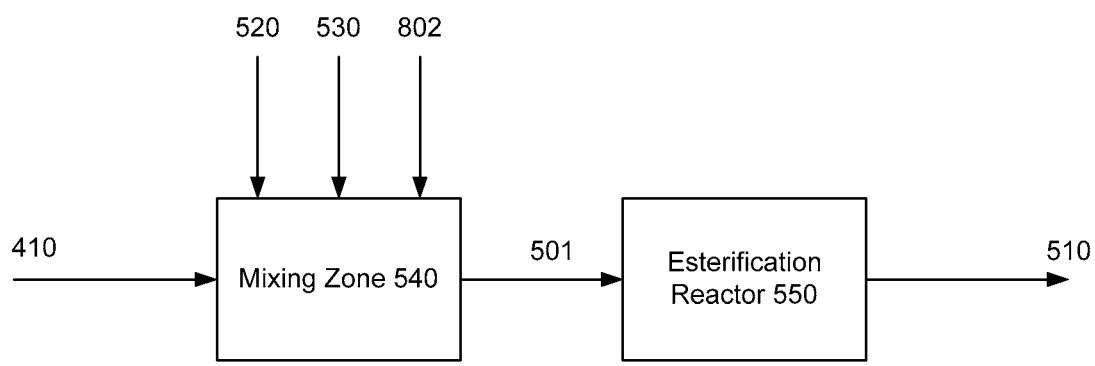
FIG. 2 is a flow diagram describing the feed of raw materials to the esterification reactor.

It is desirable to first mix the solid dicarboxylic acid composition with the alcohol prior to conducting an esterification reaction under esterification conditions. As illustrated in FIG. 2, there is provided a mixing zone 540 and esterification reactor 550 within the esterification zone 500. The solid dicarboxylic acid composition 410 comprising FDCA, an fresh or virgin feed of an alcohol composition as stream 520, optionally an alcohol recycle stream 802 comprising a recycled alcohol at least one of which is the same type of compounds as fed in stream 520, an optional esterification catalyst composition stream 530, are fed into the mixing zone 540 to generate mixed reactor feed stream 501. In one embodiment, streams 802 and 520 comprise methanol.

Mixing in zone 540 may be accomplished by any equipment known in the art for mixing liquid and solids, such as continuous in line static mixers, batch agitated vessels, and or continuous agitated vessels, and the like. The theoretical amount of alcohol required for the reaction with each mole of FDCA is two moles. The total amount of alcohol present in the esterification reactor 550 is desirably in excess of the theoretical amount required for the esterification reaction.

For example, the molar ratio of alcohol to FDCA moles ranges from greater than 2:1, or at least 2.2:1, or at least 2.5:1, or at least 3:1, or at least 4:1, or at least 8:1, or at least 10:1, or at least 15:1, or at least 20:1, or at least 25:1, or at least 30:1 and can go as high as 40:1. Suitable molar ratios are within a range of alcohol to FDCA from 10:1 to 30:1.

To the mixing zone is also optionally fed an esterification catalyst system as stream 530 if a catalyst is used. The catalyst is can be heterogeneous in a fixed bed or desirably a homogenous catalyst under esterification reaction conditions, and can also be homogeneous in the mixing zone. Known organometallic esterification catalysts can be used such as the acetate of cobalt, copper and manganese, and zinc in amounts conventionally used for esterifying terephathalic acid. Other organic catalysts can be employed such as sulfuric acid Suitable quantities of esterification catalyst range from 0.1 wt. % to 5.0 wt. %, or 0.5 wt. % to 2.0 wt. %, based on the weight of DAFD feed.

The mixed reactor feed stream 501 is routed to esterification reactor 550 to generate a crude diester composition exiting the esterification reactor as liquid crude diester stream 510. The crude diester composition, before separation of alcohol and water, desirably contains DAFD present in an amount of at least 5 wt %, or at least 8 wt. %, or at least 10 wt. %, or at least 15 wt. %, or at least 20 wt. %, and up to 40 wt. %, or up to 35 wt. %, based on the liquid phase weight of the crude diester composition. At the high temperatures, high pressure, and/or high alcohol concentration in esterification conditions, the DAFD present in the crude diester composition is solubilized and the solids concentration is generally not more than 5 wt. %, or not more than 2 wt. %, or not more than 1 wt. %, or not more than 0.5 wt. %, or not more than 0.1 wt. %, although the amount of solids can be higher as the concentration of unreacted alcohol is diminished and the reaction temperature is reduced. If solids are present, at least 99 wt. % of the solids are unreacted FDCA solids.

The yield of DAFD in the crude diester composition desirably high. Suitable yields are at least 55 mole %, or at least 60 mole %, or at least 65%, or at least 70 mole %, or at least 75 mole %, or at least 80 mole %, or at least 85 mole %, or at least 90 mole %, or at least 95 mole %, or at least 99 mole %. The yield of DAFD in the crude diester stream is calculated as follows:

mol of DAFD in the crude diester composition in the liquid phase/starting mol of FDCA)*100%.

The FDCA slurry stream can be fed into the esterification reactor at a rate corresponding to a desired throughput in a continuous process for the production of a purified DAFD product composition. Examples of suitable rates for the production of a purified DAFD product composition stream include an average of at least 1000 kg/day, or at least 10,000 kg/day, or at least 20,000 kg/day, or at least 50,000 kg/day, or at least 75,000 kg/day, or at least 100,000 kg/day, or at least 200,000 kg/day of a purified DAFD product composition, on a 24 hour basis over the course of any three months.

Esterification may be accomplished in batch or continuous reactors and comprises one or multiple reaction vessels that are capable of providing acceptable reaction residence time, temperature, and pressure. The esterification reaction residence time ranges from 0.5 hr to about 10 hours. The esterification temperature ranges from 150° C. to below the supercritical temperature of the alcohol selected to ensure that the alcohol stays in liquid phase at reaction pressures. Suitable reaction temperatures can range from 150° C. to 250° C., or 150° C. to 240° C., or from 200° C. to 230° C. Particularly suitable is an upper range of 240° C. in the case methanol is used as the alcohol. The esterification pressure within the esterification reactor is sufficient to maintain the alcohol compound in the liquid phase and will vary with the temperature selected. Suitable pressure ranges are from about 250 psig to about 2000 psig, or from 400 psig to 1500 about psig.

The crude diester composition is taken from the esterification reactor 550 as stream 510. As shown in FIG. 1, the crude diester composition stream 510 is fed to an alcohol separation zone 600. At least a portion of alcohol compound in the crude diester composition 510 is separated from the crude diester stream in the alcohol separation zone 600 in a physical separation process to produce a DAFD rich composition stream 620 containing liquid DAFD, and in which the concentration of DAFD in the DAFD rich composition, on a liquid basis, is higher than the concentration of DAFD in the crude diester composition on a liquid basis.

The crude diester composition 510 exits the esterification zone 500 at elevated temperatures, typically at a temperature of at least 150° C., or at least 170° C., or at least 180° C., or at least 190° C., or at least 200° C., or at least 210° C., or at least 220° C., or at least 230° C., or at least 240° C., and in each case below the supercritical temperature of the alcohol. To take advantage of the sensible heat energy already present in crude diester composition, one may simply conduct the physical separation under a pressure that is lower relative to the pressure over the crude diester stream upon entry into the separation zone, and thereby take off alcohol through reduced pressure to produce a DAFD-rich composition as stream 620. This can be accomplished without applying additional heat energy to the separation vessel for separation purposes and thereby reduces energy consumption (e.g. adiabatic flash).

The alcohol separation zone 600 can comprise one or more vessels operated in series or parallel. For example, the alcohol separation zone 600 can comprise one or more evaporative flash unit operations, or can comprise one or more distillation columns. The alcohol separation zone can comprise both a flash evaporation unit and a distillation column. The separation zone may be operated in a batch or continuous mode.

Desirably, the separation zone 600 contains at least a flash evaporation unit such as a flash tank. One may conduct staged flash evaporation in multiple vessels. The pressure in the flash unit operation can range from 0 psig to about 150 psig, or from 0 psig to about 50 psig, or from 0 psig to 35 psig. If alcohol is separated under a reduced pressure relative to the pressure of the crude diester composition at the entry to the physical separation vessel, it is desirable that the pressure within the alcohol separation vessel is below the vapor pressure of the alcohol at the temperature of the crude diester stream at the entry port to the alcohol separation vessel.

If desired, one does not have to first employ a flash evaporative unit. For example, the crude diester composition stream 510 can be fed directly to a distillation column, heat energy is applied if necessary to separate the alcohol from the crude diester composition, and the distillate alcohol can be taken off as gaseous overhead, condensed and sent to the esterification zone as recycle stream 802. The bottoms of the distillation column are taken off as a DAFD rich composition stream 620.

An alternative physical separation techniques is a membrane separation unit operation, which can be used alone or combination with at least one flash unit operation, to generate alcohol gas composition stream 610 and a DAFD rich composition stream 620.

The temperature of the DAFD rich composition stream 620 exiting the alcohol separation zone 600 is not particularly limited. It will be lower than the temperature of the crude diester stream entering the alcohol separation zone if evaporative separation techniques that do not apply external heat energy are used for the separation, such as a flash tank, due to evaporative cooling. However, if distillation techniques are used, the temperature of the DAFD rich composition can be the same or higher than the crude diester stream. In one embodiment, the temperature of the DAFD rich composition stream 620 is at least 5° C. cooler, or at least 20° C. cooler, or at least 50° C. cooler, or at least 75° C. cooler, or at least 100° C. cooler, or at least 120° C. cooler than the crude diester composition temperature entering the alcohol separation zone 600. If distillation is used, the DAFD rich composition stream 620 can be at least 5° C. hotter, or at least 10° C. hotter than the temperature of the crude diester composition stream feed to the distillation column.

The alcohol that is flash evaporated or distilled exits the flash tank as an alcohol gas composition stream 610. The alcohol gas composition is desirably taken as an overhead. As alcohol is flash evaporated, the concentration of DAFD increases to form a DAFD rich stream. The concentration of water also increases in the DAFD rich stream relative to the concentration of water in the crude diester composition. Since the solubility of DAFD in water is much less than DAFD in alcohol, a minor portion (e.g. less than 20 wt %) of the DAFD may precipitate out of solution. The alcohol gaseous overhead comprises alcohol, some water, and typically some very small (e.g. less than 0.1 wt %) DAFD can also be present.

The alcohol gas stream 610 can be condensed in the alcohol recovery zone 800 and fed back to the esterification zone 500 as an alcohol recycle stream 802. This recycle stream may, however, contain some amount of water. If one desires to purify the alcohol gaseous stream 610 prior to recycling to esterification zone 500, it can be fed to at least one distillation column in the alcohol recovery zone 800 to separate the alcohol compound as a distillate and recycled back to the esterification zone 500, or used as a portion or all of the wash composition 732 to the solid liquid separation zone(s), or used as a portion or all of the solvent feed 1010 to the dissolving zone(s), or a combination of any of the foregoing feeds. The distillation column can be dedicated to receive a feed of the alcohol gaseous stream or the condensed alcohol effluent. The distillation column is operated to separate water from alcohol to feed the esterification zone with the alcohol distillate as stream 802. The alcohol recycle stream 802 is desirably condensed to a liquid before feeding it to the mixing zone 540 or the esterification reactor 550.

Alternatively, the alcohol gaseous stream 610, or its condensate, can be fed to a shared distillation column in alcohol recovery zone 800 that also receives feed 721, 741 and/or 742. It is desired to used a shared column to reduce capital costs. As shown in FIG. 1, a portion of all of stream 721 can be fed first to a distillation column in alcohol recovery zone 800.

The alcohol recycle stream 802 desirably contains less than 4 wt. % water, or less than 2 wt. % water, or less than 1 wt. % water, based on the weight of the alcohol recycle stream 802. In one embodiment, alcohol recycle stream 802 comprises methanol in an amount of at least 95 wt. %, or at least 98 wt. %, or at least 99 wt. %. Water composition stream 801 is a liquid bottoms composition from a distillation column comprising water and DAFD. A portion of the water composition stream 801, up to 100 wt %, can be routed from the process. A portion of the water composition steam 801, up to 100 wt %, can be recycled within the process to recover at least a portion of the DAFD in stream 801. A portion of the water composition stream 801, up to 100 wt %, can be added to the DAFD rich stream 620 or sent to purification zone 700. The DAFD rich composition stream 620 comprises DAFD in a higher concentration that the amount of DAFD present in the crude diester stream exiting the esterification zone 500. The concentration of DAFD in the DAFD rich stream can be increased by at or at least 20%, or at least 30%, or at least 40%, or at least 50%, or at least 70%, or at least 90%, or at least 100%, or at least 150%, or at least 200%, or at least 250%, or at least 300%, or at least 400%, or at least 500%, over the concentration of DAFD in the crude diester composition. The DAFD rich stream desirably contains DAFD present in an amount of at least- or at least 10 wt %, or at least 20 wt %, or at least 30 wt %, or at least 40 wt %, or at least 50 wt %, or at least 60 wt %, and in each case up to 70 wt. %, or up to 80 wt. %, in each case based on the weight of the DAFD rich composition. The DAFD rich stream desirably contains no solids. If present, the solids comprise DAFD and/or unreacted FDCA. The solids concentration in the DAFD composition may contain no more than 55 wt. %, or up to 45 wt. %, or up to 35 wt. %, or up to 28 wt. %, or up to 15 wt. %, and if present, an amount of greater than zero, or at least 5 wt. %, or at least 10 wt. %, each based on the weight of the DAFD rich composition.

The DAFD rich composition stream 620 also contains any alcohol that did not separate in the alcohol separation zone 600, water, and a quantity of some or all of the by-products mentioned above. The amount of alcohol in the DAFD rich stream can be at least 5 wt. %, or at least 10 wt. %, or at least 15 wt. %, and up to 60 wt. %, or up to 50 wt. %, or up to 40 wt. %, based on the weight of the DAFD rich stream.

The DAFD rich composition depicted as stream 620 is fed to a purification zone 700. In the purification zone 700, the solids in the DAFD rich composition is fed to a solid liquid separation zone, where they are separated from the mother liquor and washed, to produce a purified DAFD product stream 710. Optionally the DAFD rich composition is crystallized before solid-liquid separation. The DAFD rich composition that is ultimately fed to the solid liquid separation zone generically includes all of the following steps: (i) a DAFD rich composition that is fed to the solid-liquid separation zone without undergoing one or more dissolution and/or crystallization steps, (ii) a DAFD rich composition that undergoes one or more dissolution and crystallization steps to produce a crystallized DAFD rich composition, and (iii) a DAFD rich composition that does not undergo dissolution but does undergo crystallization to produce a crystallized DAFD composition.

Figure 3:
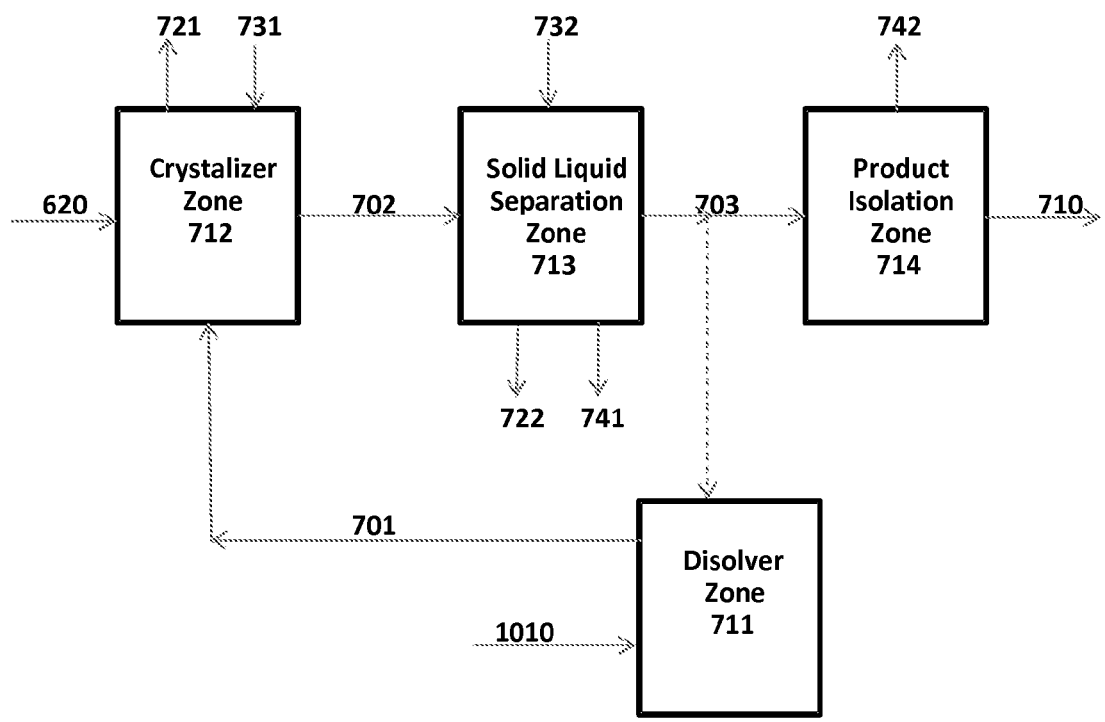
FIG. 3 is a flow diagram depicting the process of crystallizing, solid liquid separation, and isolating a DAFD composition, and optionally dissolving and subjecting the dissolved composition again to crystallization.

The purification zone 700 comprises at least a solid-liquid separation zone 713 as shown in FIG. 3. If desired, the purification zone may also comprise a crystallization zone 712, a dissolver zone 711, or both a dissolver 711 and crystallization zone 712.

A portion of the purified DMFD composition stream 703 can optionally be fed to an optional dissolver zone 711 along with an amount of a solvent stream 1010 sufficient to redissolve at least a portion of the DAFD solids in the purified DMFD composition. The solvent stream can be any solvent effective to dissolve DAFD solids, including a fresh feed of alcohol or a recycle feed of alcohol 802 obtained from the alcohol recovery zone 800.

In the dissolving zone 711, at least a portion of solids present in the purified DAFD composition 703 are dissolved. The purpose for re-dissolution of the solids after already having been subjected to solid/liquid separation in zone 713 is to further purify the DAFD solids if the level of by-products and impurities trapped within the solids after only one pass through the crystallizers remains undesirably high. By dissolution, such trapped by-products and impurities are liberated back into solution.

The amount of solvent 1010 fed to the dissolving zone is dependent upon the amount of solids one desires to dissolve, the solids concentration of the purified DAFD composition, the temperature within the dissolution zone, and the type of solvent used. It is desired to use sufficient solvent under operating conditions effective to reduce the solids concentration by at least 80%, or at least 90%, or at least 95%, or at least 98%, or at least 99%, or by 100%.

As shown in FIG. 3, the DAFD rich stream 620 is fed to a crystallization zone 712. If a dissolution process is employed, the product of the dissolution zone, a dissolved DAFD rich composition 701, can be fed to the crystallizer zone 712. The crystallization zone will generate a crystallized DAFD stream 702 comprising DAFD solids. At least a portion of DAFD in the DAFD rich stream 620, and at least a portion of the DAFD dissolved in the dissolved DAFD rich composition stream 701, comes out of solution to generate solid DAFD in crystallizer zone 712. In one embodiment, at least 80 wt. %, or at least 90 wt. %, or at least 95 wt. %, or at least 98 wt. % of DAFD in the DAFD rich composition 620 comes out of solution to form DAFD solids in crystallized DAFD stream 702. In another embodiment, at least 80 wt. %, or at least 90 wt. %, or at least 95 wt. %, or at least 98 wt. % of DAFD in the DAFD rich composition 620 and dissolved DAFD rich composition stream 701 combined comes out of solution to form DAFD solids in crystallized DAFD stream 702.

Crystallization of DMFD in crystallization zone 712 may be accomplished by any crystallizer design know in the art. Examples include forced-circulation evaporative crystallizer, forced-circulation baffle surface-cooled crystallizer, draft-tube baffle crystallizer, or direct-contact refrigeration crystallizer. The crystallization zone contains at least one crystallizer, and may contain multiple crystallizers, e.g. 2-5 in series or multiple parallel trains. Generating DMFD solids from the optional dissolved DAFD rich composition 701, or from the DAFD rich composition 620, in crystallizer zone 712 comprises cooling and/or adding an anti-solvent, and/or removing a portion of the liquid continuous phase comprising the solvent (e.g. alcohol). If solvent is removed in crystallization zone 712 by evaporation, optionally under vacuum (e.g. lower than 1 atm), as an crystallizer alcohol vapor stream 721, it can be recycled directly back to the esterification zone 500, or it can be sent to the alcohol separation zone 800 for further purification before feeding it to the esterification zone 500, or it can be used as a wash stream in the solid-liquid separation zone directly or after passing through the alcohol separation zone 800.

The operating temperature of the liquid within the crystallization vessel can range from about 5° C. to about 100° C., or 15° C. to 65° C., or 15° C. to about 35° C. The crystallization temperature can be staged downward with each successive vessel if multiple vessels.

If desired, an anti-solvent composition stream 731 can be fed to a crystallizer in the crystallization zone 712. The anti-solvent composition is a liquid that promotes crystallization and/or precipitation of DAFD under the operating conditions in the crystallizer. Such a stream can comprise water in an amount of at least 50 wt. %, or at least 60 wt. %, or at least 70 wt. %, or at least 80 wt. %, or at least 90 wt. %, or at least 98 wt. %, or 100 wt. %, based on the weight of the anti-solvent stream 731. The solubility of DMFD in methanol and water varying temperature points ranging from about 1° C. to about 61° C. are set forth in Tables 3 and 4. DMFD has very low solubility in water compared to methanol so it operates as an excellent anti-solvent to promote crystallization.

From 1% to 45%, or from 3% to 35%, of the liquid in the DAFD rich stream 620, and if present, in the dissolved DAFD rich composition stream 701, is removed by evaporation from the crystallization vessel in crystallizer zone 712. If desired, any combination of the cooling and or addition of anti-solvent may be used, along with removing a portion of the liquid continuous phase.

The crystallized DAFD composition 702 comprises solids at a concentration of at least 5 wt. %, or at least 10 wt. %, or at least 15 wt. %, or at least 20 wt. %, and up to one's ability to pump the slurry, such as about up to 50 wt. %, or up to about 45 wt. %. The solids comprise DAFD and the amount of DAFD present in the solids improves as one takes off a portion of the purified DAFD composition to cycle in a dissolution and additional crystallization cycles. The amount of DAFD present in the solids is at least 90 wt. %, or at least 95 wt. %, or at least 98 wt. %, or at least 99 wt. %, or at least 99.5 wt. %, or at least 99.7 wt. %, or at least 99.8 wt. %, or at least 99.9 wt. %, or at least 99.95 wt. %, or at least 99.97 wt. %, or at least 99.985 wt. %, or at least 99.99 wt. %, based on the weight of the crystallized DAFD composition.

The crystallized DMFD stream 702 produced in the crystallization zone 712 is fed to a solid-liquid separation zone 713. To the solid-liquid separation zone 713 is fed a wash solvent stream 732. A mother liquor stream 722, wash liquor stream 741 comprising wash solvent, and purified DAFD stream 703 are generated in the solid-liquid separation zone 713.

Solid-liquid separation zone 713 comprises at least one solid-liquid separation device capable of separating solids and liquids, washing solids with a wash stream 732, and reducing the percent moisture in the washed solids to less than 50 wt. %, or less than 40 wt. %, or less than 30 weight %, or less than 20 weight %, less than 15 weight %, and preferably less than 10 weight % based on the weight of the purified DAFD composition stream 703.

The solid-liquid separation zone generates an esterification mother liquor stream 722 containing the solvent (e.g. alcohol) and by-products and impurities. Desirably, the alcohol in esterification mother liquor stream 722 comprises methanol. Examples of by-products, or impurities, in mother liquor stream 722 comprise oxidation and or esterification by-products. If desired, at least a portion of esterification mother liquor stream 722 can be directly fed back to the esterification reaction zone 500. From 5% to 95%, from 30% to 90%, or from 40% to 80% of esterification mother liquor present in the crystallized DAFD stream fed to the solid-liquid separation zone 713 is isolated in the esterification mother liquor stream 722. The esterification mother liquor stream 722 contains dissolved impurities removed from the feed to the solid liquid separation zone 713.

The wash stream 732 fed to and used as the wash feed for the crystallized DAFD composition, comprises a liquid suitable for displacing and washing mother liquor from the solids. For example, the wash solvent may comprise water, alcohol, or water and alcohol, although the solvent is not limited to the use of alcohols. It is desirable that the wash solvent contain a solvent miscible with the remaining alcohol in the crystallized DAFD composition, and can even be the same alcohol compound. The wash solvent stream can comprise an alcohol present in an amount of at least 5 wt. %, or at least 10 wt. %, or at least 20 wt. %, or at least 40 wt. %, or at least 60 wt. %, or at least 80 wt. %, or at least 90 wt. %, or at least 95 wt. % and the remainder, if any, can be water. A mixture of alcohols can also be used.

The temperature of the wash solvent fed to the solid liquid separation zone is not limited, and can range from 10° C. up to below the boiling point of the wash solvent composition, or up to 50° or up to 40° C. The amount of wash solvent used is defined as the wash ratio and equals the mass of wash divided by the mass of solids on a batch or continuous basis. The wash ratio, defined as the ratio of wash mass divided by the mass of solids being washed, can range from 0.25 to 5, 0.3 to 4, and 0.4 to 4. If desired, no wash is applied to solids in the solid liquid separation zone 713.

The wash liquor stream 741 comprising at least a portion of the wash solvent and at least a portion of by-products is either purified and recycled or exits the process as a waste stream.

Equipment suitable for solid liquid separation can include centrifuges of all types including but not limited to decanter and disc stack centrifuges, solid bowl centrifuges, cyclone, rotary vacuum drum filter, vacuum belt filter optionally containing continuous co-current or countercurrent washing steps, pressure leaf filter, candle filter, and the like. The preferred solid liquid separation device for the solid liquid separation zone is a continuous pressure drum filter optionally with multi-stage continuous co-current or countercurrent washing, or more specifically a continuous rotary pressure drum filter. The solid-liquid separator may be operated in continuous or batch mode, although it will be appreciated that for commercial processes, the continuous mode is preferred.

One or more washes may be implemented in solid-liquid separation zone 713. In one embodiment, one or more of the washes, preferably at least the final wash, in solid-liquid separation zone 713 may comprise a difunctional hydroxyl compound, such as ethylene glycol. By this method, a purified DAFD composition wet cake stream 703 is produced comprising the same hydroxyl functional compound in liquid form that would be used in polymerization to make polyester containing FDCA moieties, and by this method, the drying step in the product isolation zone 714 can be avoided. However, if one desires to produce a dried powder, then the wash liquids desirably are solvents that can easily volatize in a drying step and effective to wash the alcohol from the DAFD. Such wash solvents include methanol, ethanol, propanol and butanol.

The functions of washing and dewatering the crystallized DAFD composition stream may be accomplished in a single solid-liquid separation device or multiple solid-liquid separation devices.

After solids are washed in the solid liquid separation zone 713, they are dewatered. Dewatering can take place in the solid-liquid separation zone, and it can be part of or a separate device from the solid liquid separation apparatus. Dewatering involves displacing and reducing at least a portion of the mass of moisture of any composition present with the solids to less than 50 wt. %, or less than 40 wt. %, or less than 30 weight %, or less than 20 weight %, less than 15 weight %, and preferably less than 10 weight % based on the weight of the purified DAFD composition stream 703. Dewatering can be accomplished by passing a gas stream through the solids to displace free liquid after the solids have been washed with a wash solvent. Alternatively, dewatering can be achieved by centrifugal forces in a perforated bowl or solid bowl centrifuge.

The purified DAFD composition stream 703 can be in the form of a wet cake. All of the purified DAFD composition can be fed to the drying zone to form dried particles or powder, or if a wet cake is desired as the final product, the drying zone can be by-passed or eliminated.

Optionally, a portion or all of the purified DAFD composition 703 can be fed to the dissolver zone 711 for dissolution and re-crystallization. As shown in FIG. 3, at least a portion of the purified DAFD composition stream 703 is taken off as a feed to the dissolver zone 711. The solids in the purified DAFD composition are redissolved in the dissolver zone 711 and the dissolved DAFD rich composition 701 is fed as a recycle loop back to the crystallization zone 712 for re-crystallization of DAFD. By this method, the concentration of DAFD in the solids is increased because a portion of the impurity by-products trapped in the DAFD solids from the purified DAFD composition 703 are liberated into solution and after another pass through the solid-liquid separation apparatus, are directed into the mother liquor stream 722. One may take off a portion of the purified DAFD composition stream 703 continuously and re-circulate a portion of the dissolved stream 701 back to the crystallization zone 712 continuously.

At least 2 wt. %, or at least 5 wt. %, or at least 10 wt. %, or at least 15 wt. %, or at least 20 wt. %, or at least 30 wt. %, or at least 35 wt. %, or at least 40 wt. %, and up to 95 wt. %, or up to 90 wt. %, or up to 85 wt. %, or up to 80 wt. %, or up to 75 wt. %, or up to 60 wt. %, or up to 50 wt. %, or up to 40 wt. %, or up to 30 wt. % of the purified DAFD composition may be taken off and fed to the dissolver zone 711.

If desired, one may take off at least a portion of the slurry from the solid liquid separation zone 713 at any point after mother liquor stream 722 has been separated from the crystallized DAFD rich composition 702. For example, a portion of the slurry may be taken off and fed to the dissolver zone 711 before the washing step in the solid liquid separation zone 713. However, it is desirable that a portion of the crystallized DAFD rich composition is taken off and fed to the dissolver zone 711 after the step of removing a mother liquor stream and after the crystallized DAFD rich composition in the solid liquid separation zone has been washed and before the final drying step in the solid liquid separation zone. In this manner, the stream has been purified of at least a portion of the by-product impurities by both separation and washing.

Figure 4:
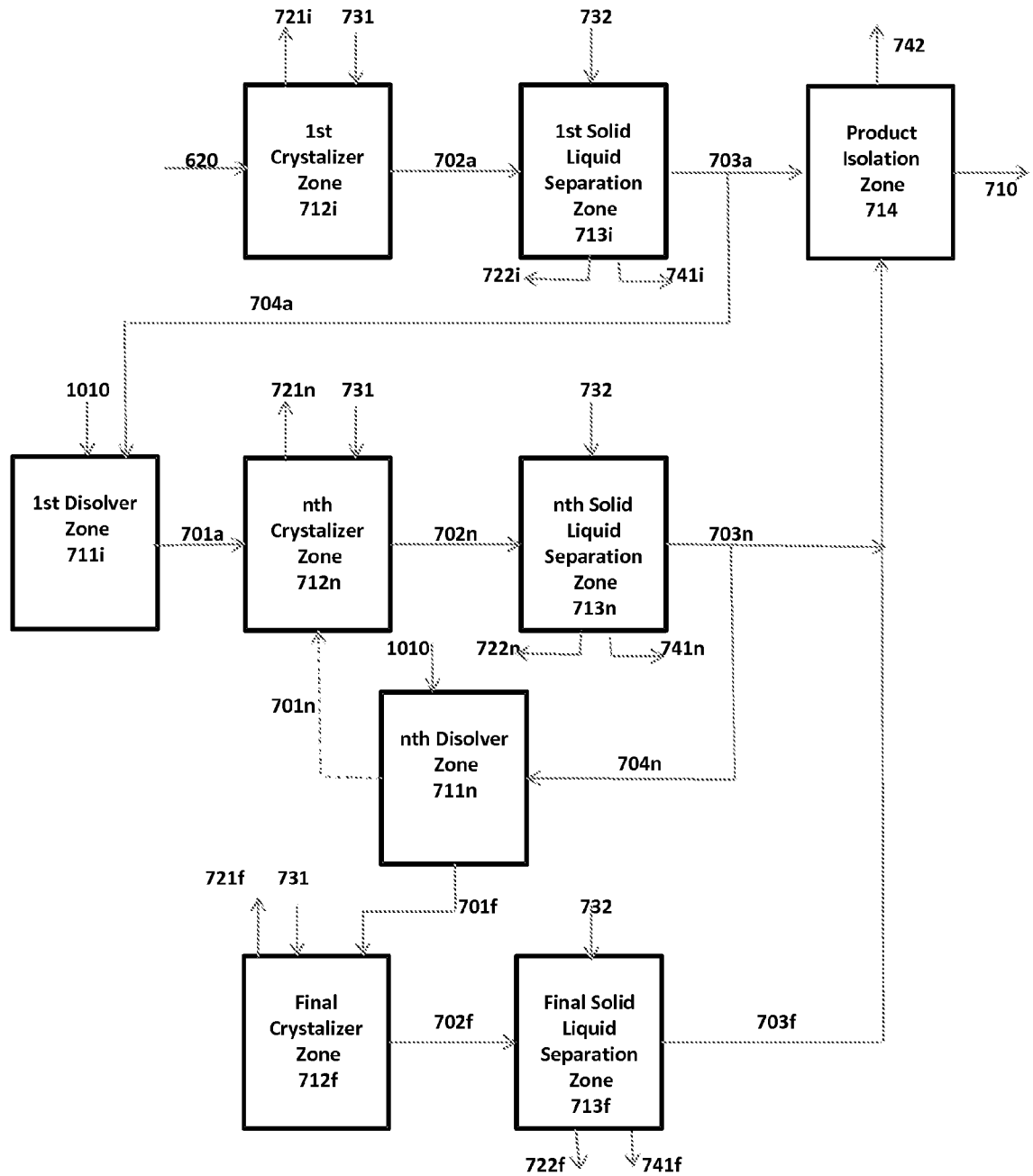
FIG. 4 is a flow diagram describing repeated stages of crystallization, solid liquid separation, and dissolution until the desired crystal purity is obtained.

If desired, the dissolved DAFD rich composition can be fed to a second crystallization zone instead of re-circulated back to the first crystallization zone 712. As shown in FIG. 4, the dissolved DAFD rich composition 701a can be fed to a $n^{th}$ crystallization zone 712 followed by feeding the $n^{th}$ crystallized DAFD composition 702n to an $n^{th}$ solid-liquid separation zone 713. This process of dissolution and recrystallization can be repeated until the desired purity is obtained. The distinction between a different zone and multiple crystallizers and/or solid liquid separation apparatus within a single zone is that a different zone is established when at least a portion of a feed composition in question is fed into two or more vessels which perform the same function. Multiple devices in series, however, do not constitute multiple zones.

As shown in FIG. 4, the DAFD rich stream 620 is fed to a first crystallization zone 712i. The product of the crystallization zone is a crystallized DAFD stream 702a comprising DAFD solids. At least a portion of DAFD in the DAFD rich stream 620 comes out of solution to generate solid DAFD in crystallizer zone 712i. Solvent can be removed from the crystallization zone 712 by evaporation, optionally under vacuum (e.g. lower than 1 atm), as a crystallizer alcohol vapor stream 721i. The crystallized DMFD stream 702a produced in the crystallization zone 712i is fed to a first solid-liquid separation zone 713i. To the solid-liquid separation zone 713i is fed a wash solvent stream 732. A first mother liquor stream 722i, a first wash liquor stream 741i comprising wash solvent, and purified DAFD composition stream 703a are generated in the solid-liquid separation zone 713i. The esterification mother liquor stream 722i contains dissolved impurities removed from the feed to the solid liquid separation zone 713i. The wash stream 732 fed to and used as the wash feed for the crystallized DAFD composition, comprises a liquid suitable for displacing and washing mother liquor from the solids. The wash liquor stream 741i comprising at least a portion of the wash solvent and at least a portion of by-products is either purified and recycled or exits the process as a waste stream. One or more washes may be implemented in solid-liquid separation zone 713i. After solids are washed in the solid liquid separation zone 713i, they are desirably dewatered. The purified DAFD composition stream 703a can be in the form of a wet cake.

As shown in FIG. 4, a portion or all of the purified DAFD composition 703a can be fed to the first dissolver zone 711i for dissolution using a solvent feed 1010 to produce a product suitable for re-crystallization. At least a portion of the purified DAFD composition stream 703a is taken off as a dissolver feed 704a to the first dissolver zone 711i. The solids in the dissolver feed 704a (a portion or all of the purified DAFD composition) are redissolved in the first dissolver zone 711i to generate a dissolved DAFD rich composition 701a that is fed into a nth crystallization zone 712n for re-crystallization of DAFD. "n" is an integer representing the number of cycles of crystallization, solid liquid separation, and dissolving, and each cycle is a nth vessel accepting a feed of material such that with each additional cycle, additional corresponding equipment is used to process the feed. The designation "n" can be an integer from 0 to 5. For example, the nth crystallizer zone 712n is a different zone from the first initial crystallizer zone 712i in that at least a portion of the dissolved DAFD rich composition 701a is fed to a different crystallization vessel within the nth crystallization zone 712n than the crystallization vessel within the first initial crystallization zone 712i. By feeding into a different crystallization vessel, a second or nth crystallization zone is established.

When n=0, the nth crystallization zone 712n and the nth solid liquid separation zone 713n and the nth dissolver zone 711n are not present and the dissolved DAFD rich composition 701a is fed into the final crystallizer zone 712f. When n=1, a third crystallization/solid liquid separation is established (the initial 712i/713i plus the n=1 plus the final 712f/713f). When n=2, then four crystallization/solid liquid separation zones are established, counting the initial and final zones, resulting if four cycles of crystallization and solid liquid separation.

Within the nth crystallization zone 712n, the dissolved DAFD rich composition 701a is crystallized using an anti-solvent composition 731 to generate a nth crystallized DAFD rich composition 702n, where n is the same integer as the "nth" integer of the nth crystallization zone 712n. The nth crystallized DAFD rich composition 702n is fed to an nth solid liquid separation zone 713n to perform solid liquid separation, washing with a wash composition 732, and optional dewatering steps and thereby generate an nth mother liquor stream 722n, an nth wash liquor stream 741n, and an nth purified DAFD composition stream 703n.

A portion of the nth purified DAFD composition stream 703n may be taken off and fed to the product isolation zone as shown in FIG. 4. A portion or all of the DAFD composition stream 703n is fed to an nth dissolver zone 711n as a nth dissolver feed 704n for dissolution of at least a portion of the DAFD solids from the purified DAFD composition stream 703n. If n is an integer greater than 1, then a portion or all of the nth dissolved DAFD rich composition 701n is fed to the nth crystallizer zone 712n. The nth dissolved DAFD rich composition feeding through line 701n will commence the next succeeding higher digit of "n" to represent the next cycle and the additional crystallizer zone and solid liquid separation zone. The number of additional crystallizer and solid liquid separation zones can be any number ranging from 0 to 5 inclusive. With each new cycle, the process steps mentioned above are repeated.

Whether or not additional crystallizer and solid liquid separation zones are established, a portion of the nth dissolved DAFD rich composition can be fed to the final crystallizer zone 712f. If no additional crystallizer/solid liquid separation zone are employed, all of the nth dissolved DAFD rich composition can be fed to the final crystallizer zone 712f. In the final crystallizer zone 712f, the dissolved DAFD rich composition is crystallized to produce a final crystallized DAFD stream 702f which is then fed to the final solid-liquid separation zone 713f to generate a final purified DAFD composition stream 703f. The final purified DAFD composition stream 703f is fed, together with any nth purified DAFD composition streams 703n if any, to the product isolation zone 714.

As shown in FIGS. 3 and 4, the purified DMFD composition stream 703, and if more than one cycle is employed, then 703a and 703f, is fed to the DMFD isolation zone 714 to produce DMFD product composition stream 710 and a vapor stream 742 comprising primarily wash solvent and if present some mother liquor. In one embodiment, DMFD isolation zone 714 comprises at least one dryer. Drying can be accomplished by any means known in the art that is capable of evaporating at least 50% of the volatiles remaining in the DMFD composition stream 703. For example, indirect contact dryers including a rotary steam tube dryer, a Single Shaft Porcupine™ dryer, and a Bepex Solidaire™ dryer may be used. Direct contact dryers including a fluid bed dryer and drying in a convey line can be used for drying. For both batch and continuous dryers, vacuum may be applied to facilitate the removal of vapor from the dryer. A rotary air lock valve may be used to continuously discharge the purified dried DMFD stream 710 from continuous dryers.

The percent solids in the DAFD product stream 710 can be at least 65 wt. %, or at least 75 wt. %, or at least 80 wt. %, or at least 85 wt. %, or at least 90 wt. %, or at least 91 wt. %, or at least 92 wt. %, or at least 93 wt. %, or at least 94 wt. %, or at least 95 wt. %, or at least 99 wt. %, or at least 99.9 wt. %, or at least 99.99 wt. %.

In one embodiment, a vacuum system can be utilized to pull vapor stream 742 from product isolation zone 714. If a vacuum system is used in this fashion, the pressure of the vapor stream 742 at the dryer outlet can range from about 760 mmHg to about 400 mmHg, from about 760 mmHg to about 600 mmHg gauge, from about 760 mmHg to about 700 mmHg, from about 760 mmHg to about 720 mmHg, or from about 760 mmHg to about 740 mmHg. The contents of the conduit between solid-liquid separation zone 713 and product isolation zone 714 utilized to transfer wet cake stream 703 comprises wet cake stream 703 and gas wherein gas is the continuous phase. The pressure at the exit of the solid liquid separation zone 703 can, if desired, be close to that of the pressure where vapor stream 742 exits product isolation zone 714, wherein the close is defined as within 2 psi, and can also be if desired within 0.8 psi, and preferably within 0.4 psi.

In another embodiment, the solids in streams 703, 703a, and 703f can be heated such that they melt and purified DMFD product stream 710 exits the process as a liquid melt without proceeding through or using a dryer.

The vapor stream 742, mother liquor stream(s) 722, 722n, 722f, and vapor stream(s) 721, 721i, and 721f all contain alcohol and can be fed to an alcohol recovery zone 800 to generate recycle alcohol stream 802, and generating a water rich bottoms stream containing water and other impurities contained within the streams 742, 722, 722i, 722f, 721, 721i, and 721f.

The DAFD product composition 710 desirably has a b* of no more than 15, or no more than 10, or no more than 5, or no more than 3, or no more than 2, or no more than 1, or no more than 0.5.

The DAFD product composition desirably has a composition profile as follows:
(i) at least 95 wt. % solids, or at least 98 wt. % solids, said solids comprising DAFD in an amount of greater than 98 wt. %, or at least 99 wt. %, or at least 99.5 wt. %, each based on the weight of the solids;
(ii) a b* of 5 or less, or 4 or less, or 3 or less, or 2 or less, and at least 0;
(iii) whether in the solid or liquid phase, not more than 3 wt. % 5-(alkoxycarbonyl)furan-2-carboxylic acid (ACFC), or not more than 2.5 wt. %, or not more than 2.0 wt. %, or not more than 1.8 wt. %, or not more than 1.5 wt. %, or not more than 1.3 wt. %, or not more than 1.0 wt. %, or not more than 0.8 wt. %, or not more than 0.6 wt. %, or not more than 0.3 wt % ACFC, or not more than 1000 ppm ACFC, or not more than 500 ppm ACFC, or not more than 250 ppm ACFC, based on the weight of the product composition, and
(iv) whether in the solid or liquid phase, not more than 3.0 wt. % alkyl 5-formylfuran-2-carboxylate (AFFC), or not more than 2.5 wt. %, or not more than 2.0 wt. %, or not more than 1.8 wt. %, or not more than 1.5 wt. %, or not more than 1.3 wt. %, or not more than 1.0 wt. %, or not more than 0.8 wt. %, or not more than 1000 ppm, or not more than 500 ppm, or not more than 250 ppm AFFC, based on the weight of the product composition; and
(v) whether in the solid or liquid phase, not more than 1 wt. % FDCA, or not more than 0.1 wt. % FDCA, or not more than 500 ppm FDCA, or not more than 100 ppm FDCA, or not more than 10 ppm FDCA, or not more than 1 ppm FDCA; and
(v) optionally not more than 1.5 wt. % water, or not more than 1.2 wt. %, or not more than 1.0 wt. %, or not more than 0.9 wt. %, or not more than 0.8 wt. %, or not more than 0.7 wt. %, or not more than 0.1 wt. %, or not more than 0.05 wt. %, or not more than 0.02 wt. % water based on the weight of the product composition.

The process of the invention is capable of improving the purity of the crude diester composition on a commercial scale. It is now possible to produce a purified DAFD product composition and DAFD product within the DAFD product composition at a rate of at least 1,000 kg/day, or at least 3000 kg/day, or at least 5,000 kg/day, or at least 10,000 kg/day, or at least 20,000 kg/day, or at least 50,000 kg/day, or at least 75,000 kg/day, or at least 100,000 kg/day, or at least 200,000 kg/day, or at least 400,000 kg/day, or at least 500,000 kg/day, on a 24 hour basis over the course of any three months.

The DAFD product composition produced at these rates desirably has a lower b*, higher DAFD concentration, and lower ACCF and AFFC concentration that each of their concentrations in the crude diester composition.

The DAFD product composition desirably has a b* that is lower than the b* of the crude diester composition by at least 1 b* unit, or at least 2 b* units, or at least 3 b* units, or at least 4 b* units, or at least 5 b* units, or at least 6 b* units.

The process of the invention is capable of improving the purity of the crude diester composition by increasing the concentration of DAFD. The DAFD product composition desirably has a higher DAFD concentration than the DAFD concentration in the crude diester composition by at least 20%, or at least 40%, or at least 50%, or at least 70%, or at least 80%, or at least 100%, or at least 120%, or at least 150%, or at least 200%, or at least 250%, or at least 300%, or at least 400%, or at least 500%, or at least 600%, or at least 700%, or at least 800%, or at least 900%, each as determined by taking the difference in the concentration between the DAFD product composition and the crude diester composition divided by the concentration of DAFD in the crude diester composition multiplied by 100, each on a weight basis. For example, final product DAFD concentration of 99 wt. %, less a DAFD concentration in crude diester composition of 15 wt. % would equal 84 wt % divided by 15 wt %=5.6×100=560% increase.

The process of the invention is capable of improving the purity of the crude diester composition by decreasing the concentration of ACFC. The DAFD product composition desirably has a lower ACFC concentration than the concentration of ACFC in the crude diester composition. The DAFD product composition desirably has an ACFC concentration that is lower than the ACFC concentration in the crude diester composition, without taking into account the presence of the alcohol, by at least 20%, or at least 40%, or at least 50%, or at least 70%, or at least 80%, or at least 90%, or at least 95%, or at least 97%, or at least 98%, or at least 99%, or at least 99.5%, as determined by taking the difference in the concentration of ACFC in the DAFD product composition and the concentration of the ACFC in the crude diester composition (calculated without taking into account the amount of alcohol present in the crude diester composition) divided by the concentration of ACFC in the DAFD product composition multiplied by 100 and each taken on a weight basis. To describe the basis of the calculation, an example is as follows: the ACFC concentration in the final product DAFD composition can be 0.02 wt % subtracted from the ACFC concentration in the crude diester composition which can be 1.2 wt % (the wt % of ACFC in the crude diester composition without accounting for the presence of alcohol)=1.18 wt % divided by 1.2 wt %=0.983× 100=98.3% reduction.

The process of the invention is capable of improving the purity of the crude diester composition by decreasing the concentration of AFFC. The DAFD product composition desirably has a lower AFFC concentration than the concentration of AFFC in the crude diester composition. The DAFD product composition desirably has an AFFC concentration that is lower than the AFFC concentration in the crude diester composition, without taking into account the presence of the alcohol, by at least 20%, or at least 40%, or at least 50%, or at least 70%, or at least 80%, or at least 90%, or at least 95%, or at least 97%, or at least 98%, or at least 99%, or at least 99.5%, as determined by taking the difference in the concentration of AFFC in the DAFD product composition and the concentration of the AFFC in the crude diester composition (calculated without taking into account the amount of alcohol present in the crude diester composition) divided by the concentration of AFFC in the DAFD product composition multiplied by 100 and each taken on a weight basis. To describe the basis of the calculation, an example is as follows: the AFFC concentration in the final product DAFD composition can be 0.03 wt % subtracted from the AFFC concentration in the crude diester composition which can be 2.8 wt % (the wt % of AFFC in the crude diester composition without accounting for the presence of alcohol)=2.77 wt % divided by 2.8 wt %=0.989× 100=98.9% reduction.

Advantageously, the esterification zone 500 is fed by a purified FDCA composition. The process for the manufacture of FDCA will now be described in more detail.

The process comprises feeding an oxidizable composition to an oxidation zone, where the oxidizable composition contains a compound having a furan moiety. The furan moiety can be represented by the structure:

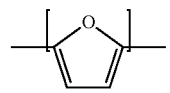

The compounds having a furan moiety are such that, upon oxidation, form carboxylic acid functional groups on the compound. Examples of compounds having furan moieties include 5-(hydroxymethyl)furfural (5-HMF), and derivatives of 5-HMF. Such derivatives include esters of 5-HMF, such as those represented by the formula 5-R(CO)OCH$_2$-furfural where R=alkyl, cycloalkyl and aryl groups having from 1 to 8 carbon atoms, or 1-4 carbon atoms or 1-2 carbon atoms; ethers of 5-HMF represented by the formula 5-R'OCH$_2$-furfural, where R'=alkyl, cycloalkyl and aryl having from 1 to 8 carbon atoms, or 1-4 carbon atoms or 1-2 carbon atoms); 5-alkyl furfurals represented by the formula 5-R"-furfural, where R"=alkyl, cycloalkyl and aryl having from 1 to 8 carbon atoms, or 1-4 carbon atoms or 1-2 carbon atoms). Thus the oxidizable composition can contain mixtures of 5-HMF and 5-HMF esters; 5-HMF and 5-HMF ethers; 5-HMF and 5-alkyl furfurals, or mixtures of 5-HMF and its esters, ethers, and alkyl derivatives.

The oxidizable composition, in addition to 5-(hydroxymethyl)furfural (5-HMF) or an of its derivatives, may also contain 5-(acetoxymethyl)furfural (5-AMF) and 5-(ethoxymethyl)furfural (5-EMF).

Specific examples of 5-HMF derivatives include those having the following structures:

Preferred 5-HMF Derivative Feeds

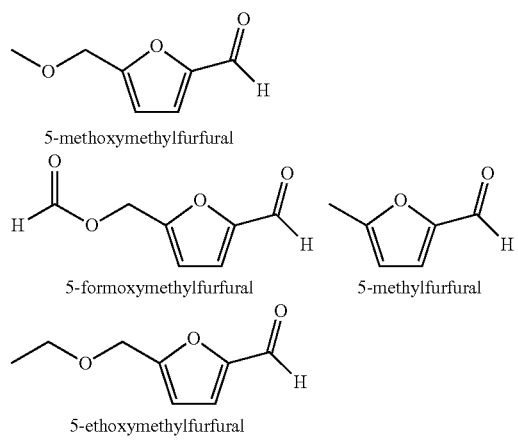

5-methoxymethylfurfural 5-formoxymethylfurfural 5-methylfurfural 5-ethoxymethylfurfural

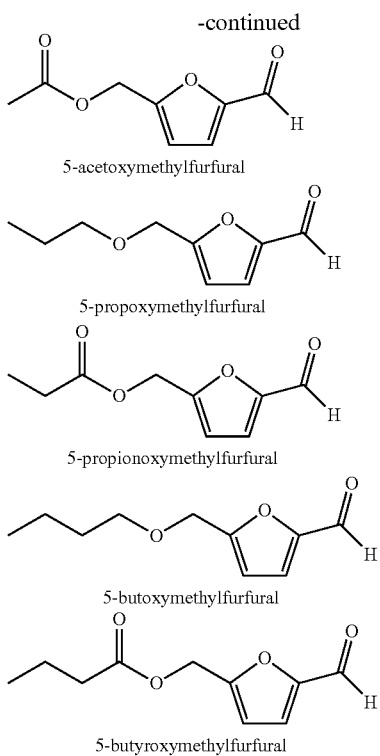

One embodiment is illustrated in FIG. 1. An oxidizable composition is fed to a primary oxidation zone 100 and reacted in the presence of a solvent, a catalyst system, and a gas comprising oxygen, to generate a crude dicarboxylic acid stream 110 comprising furan-2,5-dicarboxylic acid (FDCA).

For example, the oxidizable composition containing 5-HMF, or its derivatives, or combinations thereof, are oxidized with elemental $O_2$ in a multi-step reaction to form FDCA with 5-formyl furan-2-carboxylic acid (FFCA) as a key intermediate, represented by the following sequence:

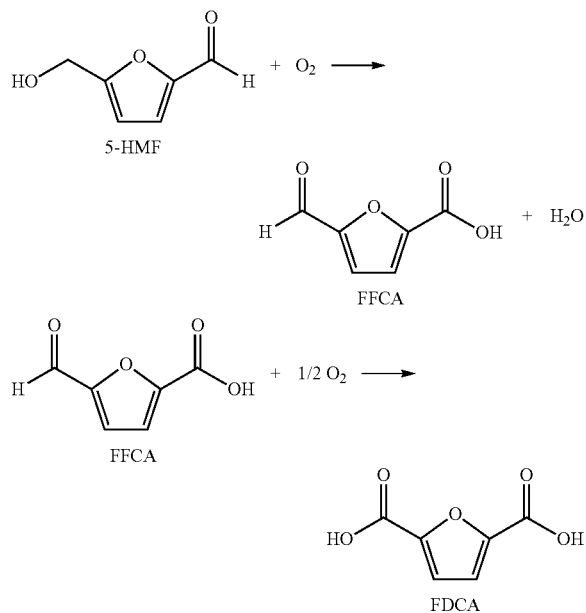

If desired, the oxygen gas stream 10 comprising oxygen, a solvent stream 30, and the oxidizable stream 20 can be fed to the primary oxidation zone 100 as separate streams. Or, an oxygen stream 10 comprising oxygen as one stream and an oxidizable stream 20 comprising solvent, catalyst, and oxidizable compounds as a second stream can be fed to the primary oxidation zone 100. Accordingly, the solvent, oxygen gas comprising oxygen, catalyst system, and oxidizable compounds can be fed to the primary oxidation zone 100 as separate and individual streams or combined in any combination prior to entering the primary oxidation zone 100 wherein these feed streams may enter at a single location or in multiple locations into the primary oxidizer zone 100.

The catalyst can be a homogenous catalyst soluble in the solvent or a heterogeneous catalyst. The catalyst composition is desirably soluble in the solvent under reaction conditions, or it is soluble in the reactants fed to the oxidation zone. Preferably, the catalyst composition is soluble in the solvent at 40° C. and 1 atm, and is soluble in the solvent under the reaction conditions.

Suitable catalysts components comprise at least one selected from, but are not limited to, cobalt, bromine and manganese compounds. Preferably a homogeneous catalyst system is selected. The preferred catalyst system comprises cobalt, manganese and bromine.

The cobalt atoms may be provided in ionic form as inorganic cobalt salts, such as cobalt bromide, cobalt nitrate, or cobalt chloride, or organic cobalt compounds such as cobalt salts of aliphatic or aromatic acids having 2-22 carbon atoms, including cobalt acetate, cobalt octanoate, cobalt benzoate, cobalt acetylacetonate, and cobalt naphthalate. The oxidation state of cobalt when added as a compound to the reaction mixture is not limited, and includes both the +2 and +3 oxidation states.

The manganese atoms may be provided as one or more inorganic manganese salts, such as manganese borates, manganese halides, manganese nitrates, or organometallic manganese compounds such as the manganese salts of lower aliphatic carboxylic acids, including manganese acetate, and manganese salts of beta-diketonates, including manganese acetylacetonate.

The bromine component may be added as elemental bromine, in combined form, or as an anion. Suitable sources of bromine include hydrobromic acid, sodium bromide, ammonium bromide, potassium bromide, and tetrabromoethane. Hydrobromic acid, or sodium bromide may be preferred bromine sources.

The amount of bromine atoms desirably ranges from at least 300 ppm, or at least 2000 ppm, or at least 2500 ppm, or at least 3000 ppm, or at least 3500 ppm, or at least 3750, ppm and up to 4500 ppm, or up to 4000 ppm, based on the weight of the liquid in the reaction medium of the primary oxidation zone. Bromine present in the an amount of 2500 ppm to 4000 ppm, or 3000 ppm to 4000 ppm are especially desirable to promote high yield.

The amount of cobalt atoms can range from at least 500 ppm, or at least 1500 ppm, or at least 2000 ppm, or at least 2500 ppm, or at least 3000 ppm, and up to 6000 ppm, or up to 5500 ppm, or up to 5000 ppm, based on the weight of the liquid in the reaction medium of the primary oxidation zone. Cobalt present in an amount of 2000 to 6000 ppm, or 2000 to 5000 ppm are especially desirable to promote high yield.

The amount of manganese atoms can range from 2 ppm, or at least 10 ppm, or at least 30 ppm, or at least 50 ppm, or at least 70 ppm, or at least 100 ppm, and in each case up to 600 ppm, or up to 500 ppm or up to 400 ppm, or up to 350 ppm, or up to 300 ppm, or up to 250 ppm, based on the weight of the liquid in the reaction medium of the primary oxidation zone. Manganese present in an amount ranging from 30 ppm to 400 ppm, or 70 ppm to 350 ppm, or 100 ppm to 350 ppm are especially desirable to promote high yield.

The weight ratio of cobalt atoms to manganese atoms in the reaction mixture can be from 1:1 to 400:1, or 10:1 to about 400:1. A catalyst system with improved Co:Mn ratio can lead to high yield of FDCA. To increase the yield of FDCA, when the oxidizable composition fed to the oxidation reactor comprises 5-HMF, then the cobalt to manganese weight ratio is at least 10:1, or at least 15:1, or at least 20:1, or at least 25:1, or at least 30:1, or at least 40:1 or at least 50:1, or at least 60:1, and in each case up to 400:1. However, in the case where the oxidizable composition comprises esters of 5-HMF, ethers of 5-HMF, or 5-alkyl furfurals, or mixtures of any of these compounds together or with 5-HMF, the cobalt to manganese weight ratio can be lowered while still obtaining high yield of FDCA, such as a weight ratio of Co:Mn of at least 1:1, or at least 2:1, or at least 5:1, or at least 9:1, or at least 10:1, or at least 15:1, or at least 20:1, or at least 25:1, or at least 30:1, or at least 40:1, or at least 50:1, or at least 60:1 and in each case up to 400:1.

The weight ratio of cobalt atoms to bromine atoms is desirably at least 0.7:1, or at least 0.8:1, or at least 0.9:1, or at least 1:1, or at least 1.05:1, or at least 1.2:1, or at least 1.5:1, or at least 1.8:1, or at least 2:1, or at least 2.2:1, or at least 2.4:1, or at least 2.6:1, or at least 2.8:1, and in each case up to 3.5, or up to 3.0, or up to 2.8.

The weight ratio of bromine atoms to manganese atoms is from about 2:1 to 500:1.

Desirably, the weight ratio of cobalt to manganese is from 10:1 to 400:1, and the weight ratio of cobalt to bromine atoms ranges from 0.7:1 to 3.5:1. Such a catalyst system with improved Co:Mn and Co:Br ratio can lead to high yield of FDCA (minimum of 90%), decrease in the formation of impurities (measured by b*) causing color in the downstream polymerization process while keeping the amount of CO and $CO_2$ (carbon burn) in the off-gas at a minimum.

Desirably, the amount of bromine present is at least 1000 ppm and up to 3500 ppm, and the weight ratio of bromine to manganese is from 2:1 to 500:1. This combination has the advantage of high yield and low carbon burn.

Desirably, the amount of bromine present is at least 1000 ppm and up to 3000 ppm, and the amount of cobalt present is at least 1000 ppm and up to 3000 ppm, and the weight ratio of cobalt to manganese is from 10:1 to 100:1. This combination has the advantage of high yield and low carbon burn.

Suitable solvents include aliphatic solvents. In an embodiment of the invention, the solvents are aliphatic carboxylic acids which include, but are not limited to, $C_2$ to $C_6$ monocarboxylic acids, e.g., acetic acid, propionic acid, n-butyric acid, isobutyric acid, n-valeric acid, trimethylacetic acid, caproic acid, and mixtures thereof.

The most common solvent used for the oxidation is an aqueous acetic acid solution, typically having a concentration of 80 to 99 wt. %. In especially preferred embodiments, the solvent comprises a mixture of water and acetic acid which has a water content of 0% to about 15% by weight. Additionally, a portion of the solvent feed to the primary oxidation reactor may be obtained from a recycle stream obtained by displacing about 80 to 90% of the mother liquor taken from the crude reaction mixture stream discharged from the primary oxidation reactor with fresh, wet acetic acid containing about 0 to 15% water.

The oxidizing gas stream comprises oxygen. Examples include, but are not limited to, air and purified oxygen. The amount of oxygen in the primary oxidation zone ranges from about 5 mole % to 45 mole %, 5 mole % to 60 mole % 5 mole % to 80 mole %.

The temperature of the reaction mixture in the primary oxidation zone can vary from about 100° C. to about 220° C. The temperature of the reaction mixture in the primary oxidation zone is at least 100° C., or at least 105° C., or at least 110° C., or at least 115° C., or at least 120° C., or at least 125° C., or at least 130° C., or at least 135° C., or at least 140° C., or at least 145° C., or at least 150° C., or at least 155° C., or at least 160° C., and can be as high as 220° C., or up to 210° C., or up to 200° C., or up to 195° C., or up to 190° C., or up to 180° C., or up to 175° C., or up to 170° C., or up to 165° C., or up to 160° C., or up to 155° C., or up to 150° C., or up to 145° C., or up to 140° C., or up to 135° C., or up to 130° C. In other embodiments, the temperate ranges from 105° C. to 180° C., or from 105° C. to 175° C., or from 105° C. to 160° C., or from 105° C. to 165° C., or from 105° C. to 160° C., or from 105° C. to 155° C., or from 105° C. to 150° C., or from 110° C. to 180° C., or from 110° C. to 175° C., or from 110° C. to 170° C., or from 110° C. to 165° C., or from 110° C. to 160° C., or from 110° C. to 155° C., or from 110° C. to 150° C., or from 110° C. to 145° C., or from 115° C. to 180° C., or from 115° C. to 175° C., or from 115° C. to 170° C., or from 115° C. to 167° C., or from 115° C. to 160° C., or from 115° C. to 155° C., or from 110° C. to 150° C., or from 115° C. to 145° C., or from 120° C. to 180° C., or from 120° C. to 175° C., or from 120° C. to 170° C., or from 120° C. to 165° C., or from 120° C. to 160° C., or from 120° C. to 155° C., or from 120° C. to 150° C., or from 120° C. to 145° C., or from 125° C. to 180° C., or from 125° C. to 175° C., or from 125° C. to 170° C., or from 125° C. to 165° C., or from 125° C. to 160° C., or from 125° C. to 155° C., or from 125° C. to 150° C., or from 125° C. to 145° C., or from 130° C. to 180° C., or from 130° C. to 175° C., or from 130° C. to 170° C., or from 130° C. to 165° C., or from 130° C. to 160° C., or from 130° C. to 155° C., or from 130° C. to 150° C., or from 130° C. to 145° C., or from 135° C. to 180° C., or from 135° C. to 175° C., or from 135° C. to 170° C., or from 135° C. to 170° C., or from 135° C. to 165° C., or from 135° C. to 160° C., or from 135° C. to 155° C., or from 135° C. to 150° C., or from 135° C. to 145° C., or from 140° C. to 180° C., or from 140° C. to 175° C., or from 140° C. to 170° C., or from 140° C. to 170° C., or from 140° C. to 165° C., or from 140° C. to 160° C., or from 140° C. to 155° C., or from 140° C. to 150° C., or from 140° C. to 145° C., or from 145° C. to 180° C., or from 145° C. to 175° C., or from 145° C. to 170° C., or from 145° C. to 170° C., or from 145° C. to 165° C., or from 145° C. to 160° C., or from 145° C. to 155° C., or from 145° C. to 150° C., or from 150° C. to 180° C., or from 150° C. to 175° C., or from 150° C. to 170° C., or from 150° C. to 165° C., or from 150° C. to 160° C., or from 150° C. to 155° C., or from 155° C. to 180° C., or from 155° C. to 175° C., or from 155° C. to 170° C., or from 155° C. to 165° C., or from 155° C. to 160° C., or from 160° C. to 180° C., or from 160° C. to 175° C., or from 160° C. to 170° C., or from 160° C. to 165° C., or from 165° C. to 180° C., or from 165° C. to 175° C., or from 165° C. to 170° C., or from 165° C. to 180° C., or from 165° C. to 175° C., or from 165° C. to 170° C., or from 170° C. to 180° C., or from 170° C. to 175° C., or from 175° C. to 180° C.

To minimize carbon burn, it is desired that the temperature of the reaction mixture is not greater than 165° C., or not greater than 160° C. In the process of the invention, the contents of the oxidizer off gas comprise COx, wherein x is 1 or 2, and the amount of COx in the oxidizer off gas is less than 0.05 moles of COx per mole of the total oxidizable feed to the reaction medium, or no more than 4 moles of COx per mole of the total oxidizable feed to the reaction medium, or no more than 6 moles of COx per mole of the total oxidizable feed to the reaction medium. The carbon burn as determined by the COx generation rate can be calculated as follows: (moles of CO+moles of CO2)/moles of oxidizable feed. The low carbon burn generation rate in the process of the invention is achievable by the combination of low reaction temperature, and the molar weight ratios of the catalyst components as described above.

The oxidation reaction can be conducted under a pressure ranging from 40 psia to 300 psia. A bubble column is desirably operated under a pressure ranging from 40 psia to 150 psia. In a stirred tank vessel, the pressure is desirably set to 100 psia to 300 psia.

Oxidizer off gas stream 120 containing COx (CO and $CO_2$), water, nitrogen, and vaporized solvent, is routed to the oxidizer off gas treatment zone 800 to generate an inert gas stream 810, liquid stream 820 comprising water, and a recovered oxidation solvent stream 830 comprising condensed solvent. In one embodiment, oxidizer off gas stream 120 can be fed to directly, or indirectly after separating condensables such as solvent from non-condensables such as COx and nitrogen in a separation column (e.g. distillation column with 10-200 trays), to an energy recovery device such as a turbo-expander to drive an electric generator. Alternatively or in addition, the oxidizer off gas stream can be fed to a steam generator before or after the separation column to generate steam, and if desired, may then be fed to a turbo-expander and pre-heated prior to entry in the expander if necessary to ensure that the off gas does not condense in the turbo-expander.

In another embodiment, at least a portion of the oxidation solvent stream 830 recovered from the oxidizer off-gas stream is routed to a filter and then to a wash solvent stream 320 to become a portion of the wash solvent stream 320 for the purpose of washing the solids present in the solid-liquid separation zone. In another embodiment, the inert gas stream 810 can be vented to the atmosphere. In yet another embodiment, at least a portion of the inert gas stream 810 can be used as an inert gas in the process for inerting vessels and or used for convey gas for solids in the process.

The oxidation can be conducted in a continuous stirred tank reactor or in a bubble column reactor.

The FDCA formed by the oxidation reaction desirably precipitates out of the reaction mixture. The reaction mixture comprises the oxidizable composition, solvent, and catalyst if a homogeneous catalyst is used, otherwise it comprises the oxidizable composition and solvent.

The product of the oxidation reaction is a crude dicarboxylic acid stream 110 comprising FDCA as a solid, FDCA dissolved in the solvent, solvent, and by-products and intermediate products, and homogeneous catalyst system if used. Examples of by-products include levulinic acid, succinic acid, and acetoxy acetic acid. Examples of intermediate products include 5-formyl furan-2-carboxylic acid (FFCA) and 2,5-diformylfuran.

The percent solids in the crude dicarboxylic acid stream ranges is at least 10 wt %, or at least 15 wt. %, or at least 20 wt. %, or at least 25 wt. %, or at least 28 wt. %, or at least 30 wt. %, or at least 32 wt. %, or at least 35 wt. %, or at least 37 wt. %, or at least 40 wt. %. While there is no upper limit, as a practice the amount will not exceed 60 wt. %, or no greater than 55 wt. %, or no greater than 50 wt. %, or no greater than 45 wt. %., or not greater than 43 wt. %, or not greater than 40 wt %, or not greater than 39 wr %.

The stated amount of each of the following intermediates, product, and impurities are based on the weight of the solids in the crude carboxylic acid composition produced in the primary oxidation reactor in the oxidation zone 100.

The amount of the intermediate FFCA present in the crude dicarboxylic acid stream is not particularly limited. Desirably, the amount is less than 4 wt. %, or less than 3.5 wt. %, or less than 3.0 wt. %, or less than 2.5 wt. %, or up to 2.0 wt. %, or up to 1.5 wt. %, or up to 1.0 wt. %, or up to 0.8 wt. %.

Impurities, if present in the crude dicarboxylic acid composition, include such compounds as 2,5-diformylfuran, levulinic acid, succinic acid, and acetoxy acetic acid. These compounds can be present, if at all, in an amount of 0 wt % to about 0.2 wt % 2,5 diformylfuran, levulinic acid in an amount ranging from 0 wt % to 0.5 wt %, succinic acid in an amount ranging from 0 wt % to 0.5 wt % and acetoxy acetic acid in an amount ranging from 0 wt % to 0.5 wt %, and a cumulative amount of these impurities in an amount ranging from 0 wt. % to 1 wt. %, or from 0.01 wt % to 0.8 wt. %, or from 0.05 wt % to 0.6 wt. %.

In another embodiment of the invention the carboxylic acid composition 110 comprises FDCA, FFCA and 5-(ethoxycarbonyl)furan-2-carboxylic acid ("EFCA"). The EFCA in the carboxylic acid composition 110 can be present in an amount of at least 0.05 wt %, or at least 0.1 wt %, or at least 0.5 wt % and in each case up to about 4 wt %, or up to about 3.5 wt %, or up to 3 wt. %, or up to 2.5 wt %, or up to 2 wt. %.

The yield of FDCA, on a solids basis and measured after the drying zone step, is at least 60%, or at least 65%, or at least 70%, or at least 72%, or at least 74%, or at least 76%, or at least 78%, or at least 80%, or at least 81%, or at least 82%, or at least 83%, or at least 84%, or at least 85%, or at least 86%, or at least 87%, or at least 88%, or at least 89%, or at least 90%., or at least 91%, or at least 92%, or at least 94%, or at least 95%, and up to 99%, or up to 98%, or up to 97%, or up to 96%, or up to 95%, or up to 94%, or up to 93%, or up to 92%, or up to 91%, or up to 90%, or up to 89%. For example, the yield can range from 70% up to 99%, or 74% up to 98%, or 78% up to 98%, or 80% up to 98%, or 84% up to 98%, or 86% up to 98%, or 88% up to 98%, or 90% up to 98%, or 91% up to 98%, or 92% up to 98%, or 94% up to 98%, or 95% up to 99%.

Yield is defined as mass of FDCA obtained divided by the theoretical amount of FDCA that should be produced based on the amount of raw material use. For example, if one mole or 126.11 grams of 5-HMF are oxidized, it would theoretically generate one mole or 156.01 grams of FDCA. If for example, the actual amount of FDCA formed is only 150 grams, the yield for this reaction is calculated to be=(150/156.01) times 100, which equals a yield of 96%. The same calculation applies for oxidation reaction conducted using 5-HMF derivatives or mixed feeds.

The product purity of FDCA particles in a wet cake, or the purity of FDCA dried solid particles, obtainable is at least 90 wt % FDCA, or at least 92 wt % FDCA, or at least 94 wt % FDCA, or at least 96 wt % FDCA, or at least 98 wt % FDCA, based on the weight of the solids.

The maximum b* of the dried solids, or wet cake, is not particularly limited. However, a b* of not more than 20, or no more than 19, or no more than 18, or no more than 17, or no more than 16, or no more than 15, or no more than 10, or no more than 8, or no more than 6, or no more than 5, or no more than 4, or no more than 3, is desirable without having to subject the crude carboxylic acid composition to hydrogenation. However, if lowered b* is important for a particular application, the crude carboxylic acid composition can be subjected to hydrogenation.

The b* is one of the three-color attributes measured on a spectroscopic reflectance-based instrument. The color can be measured by any device known in the art. A Hunter Ultrascan XE instrument is typically the measuring device. Positive readings signify the degree of yellow (or absorbance of blue), while negative readings signify the degree of blue (or absorbance of yellow).

In the next step, which is an optional step, the crude dicarboxylic acid stream 110 can fed to a cooling zone 200 to generate a cooled crude dicarboxylic acid slurry stream 210 and a $1^{st}$ solvent vapor stream 220 comprising solvent vapor. The cooling of crude carboxylic slurry stream 110 can be accomplished by any means known in the art. Typically, the cooling zone 200 is a flash tank. All or a portion of the crude dicarboxylic acid stream 110 can be fed to the cooling zone.

All or a portion of the crude dicarboxylic acid stream 110 can be fed to solid-liquid separation zone 300 without first being fed to a cooling zone 200. Thus, none or only a portion can be cooled in cooling zone 200. The temperature of stream 210 exiting the cooling zone can range from 35° C. to 160° C., 55° C. to 120° C., and preferably from 75° C. to 95° C.

The crude dicarboxylic acid stream 110, or 210 if routed through a cooling zone, is fed to a solid-liquid separation zone 300 to generate a crude carboxylic acid wet cake stream 310 comprising FDCA. The functions of isolating, washing and dewatering the crude carboxylic acid stream may be accomplished in a single solid-liquid separation device or multiple solid-liquid separation devices. The solid-liquid separation zone 300 comprises at least one solid-liquid separation device capable of separating solids and liquids, washing solids with a wash solvent stream 320, and reducing the % moisture in the washed solids to less than 30 weight %. Desirably, the solid-liquid separation device is capable of reducing the % moisture down to less than 20 weight %, or less than 15 weight %, and preferably 10 weight % or less. Equipment suitable for the solid liquid separation zone can typically be comprised of, but not limited to, the following types of devices: centrifuges of all types including but not limited to decanter and disc stack centrifuges, solid bowl centrifuges, cyclone, rotary drum filter, belt filter, pressure leaf filter, candle filter, and the like. The preferred solid liquid separation device for the solid liquid separation zone is a continuous pressure drum filter, or more specifically a continuous rotary pressure drum filter. The solid-liquid separator may be operated in continuous or batch mode, although it will be appreciated that for commercial processes, the continuous mode is preferred.

The temperature of crude carboxylic acid slurry stream, if cooled as stream 210, fed to the solid-liquid separation zone 300 can range from 35° C. to 160° C., 55° C. to 120° C., and is preferably from 75° C. to 95° C. The wash stream 320 comprises a liquid suitable for displacing and washing mother liquor from the solids. For example, the wash solvent comprises acetic acid, or acetic acid and water, an alcohol, or water, in each case up to an amount of 100%. The temperature of the wash solvent can range from 20° C. to 180° C., or 40° C. and 150° C., or 50° C. to 130° C. The amount of wash solvent used is defined as the wash ratio and equals the mass of wash divided by the mass of solids on a batch or continuous basis. The wash ratio can range from about 0.3 to about 5, about 0.4 to about 4, and preferably from about 0.5 to 3.

After solids are washed in the solid liquid separation zone 300, they are dewatered. Dewatering can take place in the solid liquid separation zone or it can be a separate device from the solid-liquid separation device. Dewatering involves reducing the mass of moisture present with the solids to less than 30% by weight, less than 25% by weight, less than 20% by weight, and most preferably less than 15% by weight so as to generate a crude carboxylic acid wet cake stream 310 comprising FDCA. Dewatering can be accomplished in a filter by passing a gas stream through the solids to displace free liquid after the solids have been washed with a wash solvent. Alternatively, dewatering can be achieved by centrifugal forces in a perforated bowl or solid bowl centrifuge.

One or more washes may be implemented in solid-liquid separation zone 300. One or more of the washes, preferably at least the final wash, in solid-liquid separation zone 300 comprises a hydroxyl functional compound as defined further below, such as an alcohol (e.g. methanol). By this method, a wet cake stream 310 is produced comprising the hydroxyl functional compound such as methanol in liquid form. The amount of the hydroxyl functional compound in liquid form in the wet cake can be at least 50 wt %, or at least 75 weight %, or at least 85% weight %, or at least 95 weight % hydroxyl functional compound such as methanol based on the weight of the liquids in the wet cake stream. The advantage of adopting this technique of washing with a hydroxyl functional compound is that a portion or all of the wet cake can be fed to the esterification zone 500 without undergoing, or by-pass, a step of feeding the wet cake to a vessel for drying the wet cake in a drying zone 400 after the solid-liquid separation zone.

In one embodiment, 100% of wet cake stream 310 is fed to esterification reaction zone 500 without undergoing or subjecting the wet cake to a vessel for drying the wet cake from the solid liquid separation zone 300.

Stream 330 generated in solid-liquid separation zone 300 is a liquid mother liquor stream comprising oxidation solvent, catalyst, and impurities. If desired, a portion of mother liquor stream 330 can be fed to a purge zone 900 and a portion can be fed back to the primary oxidation zone 100, wherein a portion is at least 5 weight % based on the weight of the liquid. Wash liquor stream 340 is also generated in the solid-liquid separation zone 300 and comprises a portion of the mother liquor present in stream 210 and wash solvent wherein the weight ratio of mother liquor mass to wash solvent mass in the wash liquor stream is less than 3 and preferably less than 2. From 5% to 95%, from 30% to 90%, and most preferably from 40% to 80% of mother liquor present in the crude carboxylic acid stream fed to the solid-liquid separation zone 200 is isolated in solid-liquid separation zone 300 to generate mother liquor stream 330 resulting in dissolved matter comprising impurities present in the displaced mother liquor not going forward in the process. The mother liquor stream 330 contains dissolved impurities removed from the crude dicarboxylic acid.

Sufficient wash solvent is fed to the solid liquid separation zone 300 that becomes mixed with solids present resulting in a low impurity slurry stream 310 being pumpable with weight % solids ranging from 1% to 50%, 10% to 40%, and preferably the weight % solids in stream 310 will range from 25% to 38%.

In one embodiment, from 5% to 100% by weight of the displaced mother liquor stream 330 is routed to a purge zone 900 wherein a portion of the impurities present in stream 330 are isolated and exit the process as purge stream 920, wherein a portion is 5% by weight or greater. Recovered solvent stream 910 comprises solvent and catalyst isolated from stream 330 and is recycled to the process. The recovered solvent stream 910 can be recycled to the primary oxidation zone 100 and contains greater than 30% of the catalyst that entered the purge zone 900 in stream 330. The stream 910 recycled to the primary oxidation zone 100 may contain greater than 50 weight %, or greater than 70 weight %, or greater than 90 weight % of the catalyst that enters the purge zone 900 in stream 330 on a continuous or batch basis.

Optionally, a portion up to 100% of the crude carboxylic acid composition may be routed directly to a secondary oxidation zone (not shown) before being subjected to a solid liquid separation zone 300.

Generally, oxidation in a secondary oxidation zone is at a higher temperature than the oxidation in the primary oxidation zone 100 to enhance the impurity removal. In one embodiment, the secondary oxidation zone is operated at about 30° C., 20° C., and preferably 10° C. higher temperature than the oxidation temperature in the primary oxidation zone 100 to enhance the impurity removal. The secondary oxidation zone can be heated directly with solvent vapor, or steam via stream or indirectly by any means known in the art.

Additional purification of the crude carboxylic acid stream can be accomplished in the secondary oxidation zone by a mechanism involving recrystallization or crystal growth and oxidation of impurities and intermediates including FFCA. One of the functions of the secondary oxidation zone is to convert FFCA to FDCA. FFCA is considered monofunctional relative to a polyester condensation reaction because it contains only one carboxylic acid. FFCA is present in the crude carboxylic acid composition stream. FFCA is generated in the primary oxidation zone 100 because the reaction of 5-HMF to FFCA can be about eight times faster than the reaction of FFCA to the desired di-functional product FDCA. Additional air or molecular oxygen may be fed to the secondary oxidation zone in an amount necessary to oxidize a substantial portion of the partially oxidized products such as FFCA to the corresponding carboxylic acid FDCA. Generally, at least 70% by weight, or at least 80 wt %, or at least 90 wt % of the FFCA present in the crude carboxylic acid composition exiting the primary oxidation zone can be converted to FDCA in the secondary oxidation zone. Significant concentrations of monofunctional molecules like FFCA in the dried, purified FDCA product are particularly detrimental to polymerization processes as they may act as chain terminators during the polyester condensation reaction.

If a secondary oxidation zone is employed, the secondary oxidation slurry can be crystallized to form a crystallized slurry stream. Vapor from the crystallization zone can be condensed in at least one condenser and returned to the crystallization zone or recycled, or it can be withdrawn or sent to an energy recovery device. The crystallizer off-gas can be removed and routed to a recovery system where the solvent is removed, and crystallizer off gas containing VOC's may be treated, for example, by incineration in a catalytic oxidation unit. The crystallizer can be operated by cooling the secondary oxidation slurry to a temperature between about 40° C. to about 175° C. to form a crystallized slurry stream.

The crystallized slurry stream can then be subjected to a cooling zone 200 if desired and the process continued as described above.

Instead of using a wet cake, one may produce a dried solid. The wet cake produced in the solid liquid separation zone 300 can be dried in a drying zone 400 to generate a dry purified carboxylic acid solid 410 and a vapor stream 420. The vapor stream 420 typically comprises the wash solvent vapor used in the solid liquid separation zone, and may additionally contain the solvent used in the primary oxidation zone. The drying zone 400 comprises at least one dryer and can be accomplished by any means known in the art that is capable of evaporating at least 10% of the volatiles remaining in the purified wet cake stream to produce the dried, purified carboxylic acid solids. For example, indirect contact dryers include, but are not limited to, a rotary steam tube dryer, a Single Shaft Porcupine dryer, and a Bepex Solidaire dryer. Direct contact dryers include, but are not limited to, a fluid bed dryer and drying in a convey line.

The dried, purified carboxylic acid solids comprising purified FDCA can be a carboxylic acid composition with less than 8% moisture, preferably less than 5% moisture, and more preferably less than 1% moisture, and even more preferably less than 0.5%, and yet more preferably less than 0.1%.

A vacuum system can be utilized to draw vapor stream 420 from the drying zone 400. If a vacuum system is used in this fashion, the pressure at the dryer outlet can range from about 760 mmHg to about 400 mmHg, from about 760 mmHg to about 600 mmHg, from about 760 mmHg to about 700 mmHg, from about 760 mmHg to about 720 mmHg, and from about 760 mmHg to about 740 mmHg wherein pressure is measured in mmHg above absolute vacuum.

The dried, purified carboxylic acid solids, or the solids in the wet cake, desirably have a b* less than about 9.0, or less than about 6.0, or less than about 5.0, or less than about 4.0. or less than about 3.

It should be appreciated that the process zones previously described can be utilized in any other logical order to produce the dried, purified carboxylic acid. It should also be appreciated that when the process zones are reordered that the process conditions may change. It is also understood that all percent values are weight percents.

One function of drying zone 400 is to remove by evaporation oxidation solvent comprising a mono-carboxylic acid with 2 to 6 carbons that can be present in the crude carboxylic acid wet cake stream 310. The % moisture in crude carboxylic acid wet cake stream 310 typically ranges from 4.0% by weight to 30% by weight depending on the operation conditions of the solid-liquid separation zone 300. If for example, the liquid portion of stream 310 is about 90% acetic acid, the amount of acetic acid present in stream 310 can range from about 3.6 weight % to 27 weight %. It is desirable to remove acetic acid prior to esterification zone 500 because acetic acid will react with the alcohol present in the zone 500 to create unwanted by products. For example, if methanol is fed to esterification zone 500 for the purpose of reacting with FDCA, it will also react with acetic acid present to form methyl acetate and therefore consume methanol and generate an unwanted by-product. It is desirable to minimize the acetic acid content of the crude carboxylic acid stream comprising FDCA that is fed to esterification zone 500 to less than 3.6 weight %, preferably less than 1 weight %, and more preferably less than 0.5 weight %, and most preferably less than 0.1 weight %. One method for achieving this is to dry a crude carboxylic acid wet cake stream 310 comprising acetic acid prior to routing the crude carboxylic to esterification zone 500. Another method for minimizing the oxidation solvent comprising mono-carboxylic acid with carbons ranging from 2 to 5 in the crude carboxylic acid stream 410 routed to esterification zone 500 to an acceptable level without utilizing a dryer zone 400 is to conduct non-monocarboxylic acid wash or washes in solid-liquid separation zone 300 to wash the oxidation solvent from the solids with a wash comprising any wash solvent compatible with the esterification zone 500 chemistry to generate a crude carboxylic acid wet cake stream 310 suitable for routing directly to esterification zone 500 without being dried in drying zone 400. Acceptable wash solvents comprise solvents that do not make undesirable by products in esterification zone 500. For example, water is an acceptable wash solvent to displace acetic acid from solids in solid-liquid separation zone 300. Another acceptable wash solvent is an alcohol that will be used as a reactant in the esterification zone 500. There can be multiple and separate washes in the solid liquid separation zone 300. A wash feed can comprise water up to 100 weight %. A wash feed can comprise an alcohol up to 100 weight %. A wash feed can comprise methanol up to 100%. A wash feed can comprise the same alcohol utilized in the esterification zone 500 for reaction with FDCA to form the di-ester product. In one embodiment, a wet cake dewatering step can be used after the wet cake is formed in the solid liquid separation zone 300 and before any non-acetic acid wash is employed. This dewatering step will minimize the liquid content of the wet cake prior to washing with a non-acetic acid wash solvent such as water and or methanol as described above, thus minimizing the cost to separate any mixtures of acetic acid and non-acetic acid wash solvents that are generated in solid-liquid separation zone 300.

The solid dicarboxylic acid composition 410, which can be either dried carboxylic acid solids or wet cake, comprising FDCA, and the alcohol composition stream 520 are fed to the esterification reaction zone 500. The solid dicarboxylic acid composition 410 can be shipped via truck, ship, or rail as solids. However, an advantage of the invention is that the process for the oxidation of the oxidizable material containing the furan group can be integrated with the process for the manufacture of the crude diester composition.

An integrated process includes co-locating the two manufacturing facilities, one for oxidation and the other for esterification, within 10 miles, or within 5 miles, or within 2 miles, or within 1 mile, or within ½ mile of each other. An integrated process also includes having the two manufacturing facilities in solid or fluid communication with each other. If a solid dicarboxylic acid composition is produced, the solids can be conveyed by any suitable means, such as air or belt, to the esterification facility. If a wet cake dicarboxylic acid composition is produced, the wet cake can be moved by belt or pumped as a liquid slurry to the facility for esterification. The process of the invention is further described in the following examples.

Example 1 and 2

Semi-Batch Oxidation of 5-HMF

Air oxidation of 5-HMF using cobalt, manganese and ionic bromine catalysts system in acetic acid solvent in the amounts shown in Table 1 were conducted under the following reaction conditions in a reactor set up as described below:
Reactor conditions: 132° C.
Reaction pressure: 130 psig
Reactor set up: a 300 ml autoclave was equipped with a high pressure condenser, a baffle and an Isco pump. The autoclave was pressurized with approximately 50 psig of nitrogen and then the homogeneous mixture was heated to the desired temperature in a closed system (i.e., with no gas flow) with stirring. At reaction temperature, an air flow of 1500 sccm was introduced at the bottom of the solution and the reaction pressure was adjusted to the desired pressure. A solution of 5-HMF in acetic acid was fed to the mixture at a rate of 0.833 mL/min via a high pressure Isco pump (this is t=0 for the reaction time). After 30 seconds from the start of 5-HMF feeding, 1.0 g of peracetic acid in 5.0 mL of acetic acid was introduced using a blow-case to start the reaction. The feed was stopped after 1 h and the reaction continued for 1 more hour at the same conditions of air flow, temperature and pressure. After the reaction time was completed the air flow was stopped and the autoclave was cooled to room temperature and depressurized. After reaction the heterogeneous mixture was filtered to isolate the crude FDCA. The crude FDCA was washed with acetic acid two times and then twice with deionized water. The washed crude FDCA was oven dried at 110° C. under vacuum overnight. The solid and the filtrate were analyzed by Gas Chromatography using BSTFA derivatization method. The b* of the solid was measured using a Hunter Ultrascan XE instrument by the following method:

1) Assemble the Carver Press die as instructed in the directions—place the die on the base and place the bottom 40 mm cylinder polished side face-up.
2) Place a 40 mm plastic cup (Chemplex Plasticup, 39.7×6.4 mm) into the die.
3) Fill the cup with the sample to be analyzed. The exact amount of sample added is not important.
4) Place the top 40 mm cylinder polished side face-down on the sample.
5) Insert the plunger into the die. No "tilt" should be exhibited in the assembled die.
6) Place the die into the Carver Press, making sure that it is near the center of the lower platen. Close the safety door.
7) Raise the die until the upper platen makes contact with the plunger. Apply >20,000 lbs pressure. Then allow the die to remain under pressure for approximately 3 minutes (exact time not critical).
8) Release the pressure and lower the lower platen holding the die.
9) Disassemble the die and remove the cup. Place the cup into a labeled plastic bag (Nasco Whirl-Pak 4 oz).
10) Using a HunterLab Colorquest XE colorimeter, create the following method (Hunterlab EasyQuest QC software, version 3.6.2 or later)
Mode: RSIN-LAV (Reflectance Specular Included-Large Area View, 8° viewing angle)
Measurements:
    CIE L* a* b*
    CIE X Y Z
11) Standardize the instrument as prompted by the software using the light trap accessory and the certified white tile accessory pressed against the reflectance port.
12) Run a green tile standard using the certified white tile and compare the CIE X, Y, and Z values obtained against the certified values of the tile. The values obtained should be ±0.15 units on each scale of the stated values.
13) Analyze the sample in the bag by pressing it against the reflectance port and obtaining the spectrum and L*, a*, b* values. Obtain duplicate readings and average the values for the report.

As shown in Table 1 we have discovered conditions to generate yields of FDCA up to 89.4%, b*<6, and low carbon burn (<0.0006 mol/min CO+CO2). 1a and 1b are repeated experiments to show the consistency and small deviation in the results. Experiments 2a and 2b are also repeated experiments.

TABLE 1

| Example | Bromide source | Co conc (ppm) | Mn conc (ppm) | Br conc (ppm) | yield of FDCA (%) | yield of FFCA (%) | CO (total mol) | $CO_2$ (total mol) | $CO_X$ (mol/min) | color (b*) |
|---|---|---|---|---|---|---|---|---|---|---|
| 1a | solid NaBr | 2000 | 93.3 | 3000 | 81.6 | 0.81 | 0.013 | 0.078 | 0.000758 | 13.91 |
| 1b | solid NaBr | 2000 | 93.3 | 3000 | 82.6 | 0.87 | 0.013 | 0.092 | 0.000875 | 14.14 |

TABLE 1-continued

| Example | Bromide source | Co conc (ppm) | Mn conc (ppm) | Br conc (ppm) | yield of FDCA (%) | yield of FFCA (%) | CO (total mol) | $CO_2$ (total mol) | $CO_X$ (mol/min) | color (b*) |
|---|---|---|---|---|---|---|---|---|---|---|
| 2a | aqueous HBr | 2000 | 93.3 | 3000 | 89.4 | 0.58 | 0.003 | 0.061 | 0.000533 | 5.85 |
| 2b | aqueous HBr | 2000 | 93.3 | 3000 | 88.6 | 0.8 | 0.0037 | 0.061 | 0.000539 | 6.18 |

*P = 130 psig, $CO_x$ (mol/min) = CO (mol/min) + CO2 (mol/min).

Example 3

Synthesis of DMFD 100.0 g of crude FDCA, obtained from a different batch than Example 1 but made by the procedure and using the feeds of Example 1 b, was used as the feedstock. This batch of FDCA contained some FFCA. 410 g of MeOH and the FDCA were mixed in a clean and dry 1 L autoclave at a molar ratio of methanol to FDCA of 20:1 and no esterification catalyst was added. The autoclave mixture was heated to 180° C. in a closed system to let the pressure develop. After 3 h at 180° C. the reaction mixture was cooled to room temperature. The volatiles were removed to obtain 114 g of crude product. GC analysis of the crude product showed the following composition: 95.64 wt % of DMFD based on the weight of reaction product, 0.50 wt % of 5-(methoxycarbonyl)furan-2-carboxylic acid (MCFC) based on the weight of product, 1.78 wt % of methyl 5-formylfuran-2-carboxylate (MFFC) based on the weight of product, and 0.74 wt % of water.

Example 4

Solubility of DMFD In Water and Methanol

The solubility of DMFD in water and methanol was tested according to the following procedure: A jacketed 120 ml solubility cells equipped with a condenser, a digital thermometer, a nitrogen blanket and connected to a circulating bath capable of heating/cooling was charged with FDCA and water or methanol. The heterogeneous mixture was heated to the desired temperature and sample was taken using preheated fritted glass pipette. The samples were analyzed using gas chromatography. The results are reported in Tables 3 and 4.

TABLE 3

Measurements of DMFD Solubility (wt %) in Methanol

| T, ° C. | wt % |
|---|---|
| 1.0 | 0.6 |
| 14.1 | 1.4 |
| 26.3 | 2.8 |
| 35.3 | 4.5 |
| 46.6 | 8.7 |
| 56.1 | 15.4 |
| 61.3 | 20.8 |

TABLE 4

Measurements of DMFD Solubility (wt %) in Water

| T, ° C. | wt % |
|---|---|
| 1.4 | BDL |
| 13.1 | BDL |
| 26.6 | BDL |
| 35.6 | BDL |
| 47.0 | 0.1 |
| 56.6 | 0.2 |
| 63.9 | 0.3 |
| 74.6 | 0.4 |
| 89.5 | 0.9 |
| 97.5 | 1.3 |

BDL, below detection limit

Example 5

Recrystallization of Crude DMFD Using Methanol

A 150 mL three neck round bottom flask equipped with an overhead stirrer, a nitrogen line and a condenser was charged with 6.0 g of FDMC and 54.0 g of methanol. The solid was dissolved by heating the mixture to 55° C. The homogenous solution was cooled to 2° C. over a period of 3 h. Then the solid was filtered and washed with 20 g methanol pre-chilled to 2° C. two times. It was dried under vacuum overnight. The same experiment was repeated at 5° C. and 10° C. The b* of each sample was measured and the results are reported in Table 5.

TABLE 5

Recrystallization of crude DMFD using cold methanol.

| | b* |
|---|---|
| crude DMFD | 5.46 |
| DMFD recrystallized at 10° C. | 1.08 |
| DMFD recrystallized at 5° C. | 0.86 |
| DMFD recrystallized at 2° C. | 0.54 |

What we claim is:
1. A dialkyl furan dicarboxylate (DAFD) composition, comprising:
   (i) at least 98 wt. % solids based on the weight of the composition, said solids comprising DAFD in an amount of greater than 98 wt. % based on the weight of the solids,
   (ii) a b* of 5 or less,
   (iii) not more than 3 wt. % 5-(alkoxycarbonyl)furan-2-carboxylic acid (ACFC),
   (iv) not more than 3 wt. % alkyl 5-formylfuran-2-carboxylate (AFFC), and
   (v) not more than 1 wt. % furan-2,5-dicarboxylic acid (FDCA).

2. The DAFD composition of claim 1, wherein the DAFD is dimethyl furan dicarboxylate (DMFD).

3. The DAFD composition of claim 2, comprising:
   (i) not more than 0.3 wt. % 5-(methoxycarbonyl)furan-2-carboxylic acid (MCFC), and
   (ii) not more than 0.8 wt. % methyl 5-formylfuran-2-carboxylate (MFFC).

4. The DAFD composition of claim 3, which comprises:
   (i) not more than 1000 ppm MCFC, and
   (ii) not more than 1000 ppm MFFC.

* * * * *